United States Patent
Hsiai et al.

(10) Patent No.: US 11,857,318 B2
(45) Date of Patent: Jan. 2, 2024

(54) ELECTROCHEMICAL IMPEDANCE SPECTROSCOPY

(71) Applicant: THE REGENTS OF THE UNIVERSITY OF CALIFORNIA, Oakland, CA (US)

(72) Inventors: Tzung K. Hsiai, Santa Monica, CA (US); Yu-Chong Tai, Pasadena, CA (US); Rene R. Sevag Packard, Los Angeles, CA (US); Yuan Luo, Pasadena, CA (US); Parinaz Abiri, Los Angeles, CA (US); Jianguo Ma, Shangdong Province (CN)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1195 days.

(21) Appl. No.: 16/099,742

(22) PCT Filed: May 9, 2017

(86) PCT No.: PCT/US2017/031779
§ 371 (c)(1),
(2) Date: Nov. 8, 2018

(87) PCT Pub. No.: WO2017/196860
PCT Pub. Date: Nov. 16, 2017

(65) Prior Publication Data
US 2019/0183392 A1    Jun. 20, 2019

Related U.S. Application Data

(60) Provisional application No. 62/490,310, filed on Apr. 26, 2017, provisional application No. 62/333,608, filed on May 9, 2016.

(51) Int. Cl.
*A61B 5/00* (2006.01)
*A61B 5/1473* (2006.01)
(Continued)

(52) U.S. Cl.
CPC .......... *A61B 5/1473* (2013.01); *A61B 5/0205* (2013.01); *A61B 5/02007* (2013.01);
(Continued)

(58) Field of Classification Search
CPC .. A61B 5/1473; A61B 5/02007; A61B 5/0205
See application file for complete search history.

(56) References Cited

U.S. PATENT DOCUMENTS 4,318,402 A * 3/1982 Vaillancourt ....... A61M 25/007
                                                      604/523
4,808,164 A * 2/1989 Hess .................. A61M 25/104
                                                      606/7

(Continued)

OTHER PUBLICATIONS

Ai, Lisong, et al. "Shear stress influences spatial variations in vascular Mn-SOD expression: implication for LDL nitration." American Journal of Physiology—Cell Physiology 294.6 (2008): C1576-C1585.

(Continued)

*Primary Examiner* — Joseph M Santos Rodriguez
(74) *Attorney, Agent, or Firm* — Riverside Law LLP

(57) ABSTRACT

The present invention provides devices for characterizing regions of tissue and methods for using the same. The devices are capable of locating, identifying, and characterizing tissue regions of interest in vivo. In one embodiment, the devices are ultrasound-guided. In one embodiment, the devices use characterize regions of tissue using electrical impedance spectroscopy (EIS) sensors. In one aspect, the devices are useful in predicting plaque rupture, such as by determining the level of oxidized low density lipoprotein (oxLDL) and macrophage/foam cells present in an (Continued)

atheroma. In one aspect, the devices are useful in identifying metabolically active atherosclerotic lesions that are angiographically invisible.

28 Claims, 24 Drawing Sheets

(51) Int. Cl.
| | |
|---|---|
| A61B 5/02 | (2006.01) |
| A61B 5/0538 | (2021.01) |
| G01N 29/06 | (2006.01) |
| G01N 29/00 | (2006.01) |
| A61B 5/0205 | (2006.01) |
| A61B 8/00 | (2006.01) |
| G01N 27/02 | (2006.01) |
| A61B 8/12 | (2006.01) |
| A61B 5/01 | (2006.01) |
| A61B 5/0215 | (2006.01) |
| A61B 5/026 | (2006.01) |
| A61B 5/0537 | (2021.01) |
| A61M 25/10 | (2013.01) |

(52) U.S. Cl.
CPC .......... A61B 5/0538 (2013.01); A61B 5/6853 (2013.01); A61B 5/7275 (2013.01); A61B 8/445 (2013.01); G01N 27/026 (2013.01); G01N 29/00 (2013.01); G01N 29/06 (2013.01); G01N 29/0654 (2013.01); A61B 5/01 (2013.01); A61B 5/026 (2013.01); A61B 5/0215 (2013.01); A61B 5/0537 (2013.01); A61B 8/12 (2013.01); A61M 2025/1079 (2013.01)

(56) References Cited

U.S. PATENT DOCUMENTS

| | | | | |
|---|---|---|---|---|
| 4,841,977 | A | * | 6/1989 | Griffith ............ A61B 8/12 29/25.35 |
| 4,911,170 | A | | 3/1990 | Thomas, III |
| 5,115,814 | A | * | 5/1992 | Griffith ............ A61B 5/06 600/439 |
| 5,190,046 | A | | 3/1993 | Shturman |
| 5,327,885 | A | | 7/1994 | Griffith |
| 5,331,947 | A | | 7/1994 | Shturman |
| 6,165,127 | A | | 12/2000 | Crowley |
| 2010/0087782 | A1 | | 4/2010 | Ghaffari |
| 2012/0078074 | A1 | | 3/2012 | Gao |
| 2013/0150693 | A1 | | 6/2013 | D Angelo et al. |
| 2013/0282084 | A1 | | 10/2013 | Mathur |
| 2014/0128859 | A1 | | 5/2014 | Lee |

OTHER PUBLICATIONS

Bamford, John, et al. "Classification and natural history of clinically identifiable subtypes of cerebral infarction." The Lancet 337.8756 (1991): 1521-1526.
Brezinski, Mark E., et al. "Assessing atherosclerotic plaque morphology: comparison of optical coherence tomography and high frequency intravascular ultrasound." Heart 77.5 (1997): 397-403.
Cao, Hung, et al. "Stretchable electrochemical impedance sensors for intravascular detection of lipid-rich lesions in New Zealand White rabbits." Biosensors and Bioelectronics 54 (2014): 610-616.
Davies, Peter F., et al. "Turbulent fluid shear stress induces vascular endothelial cell turnover in vitro." Proceedings of the National Academy of Sciences 83.7 (1986): 2114-2117.
Doyle, Brendan, and Noel Caplice. "Plaque neovascularization and antiangiogenic therapy for atherosclerosis." Journal of the American College of Cardiology 49.21 (2007): 2073-2080.

Elliott, M. R., and A. J. Thrush. "Measurement of resolution in intravascular ultrasound images." Physiological measurement 17.4 (1996): 259.
Fayad, Z. A., and V. Fuster. "Clinical imaging of the high-risk or vulnerable atherosclerotic plaque." Circulation research 89.4 (2001): 305-316.
Finn, Aloke V., et al. "Concept of vulnerable/unstable plaque." Arteriosclerosis, thrombosis, and vascular biology 30.7 (2010): 1282-1292.
Gessner, Ryan, et al. "High-resolution, high-contrast ultrasound imaging using a prototype dual-frequency transducer: in vitro and in vivo studies." IEEE transactions on ultrasonics, ferroelectrics, and frequency control 57.8 (2010): 1772-1781.
Gessner, Ryan C., et al. "Acoustic angiography: a new imaging modality for assessing microvasculature architecture." International journal of biomedical imaging 2013 (2013).
Hwang, Juliana, et al. "17β-Estradiol reverses shear-stress-mediated low density lipoprotein modifications." Free Radical Biology and Medicine 41.4 (2006): 568-578.
Jaffer, Farouc A., et al. "Clinical Perspective." Circulation 118.18 (2008): 1802-1809.
Jansen, Krista, et al. "Intravascular photoacoustic imaging of human coronary atherosclerosis." Optics letters 36.5 (2011): 597-599.
Khurana, Rohit, et al. "Role of angiogenesis in cardiovascular disease: a critical appraisal." Circulation 112.12 (2005): 1813-1824.
Kim, Dae-Hyeong, et al. "Epidermal electronics." science 333.6044 (2011): 838-843.
Larsson, Jonas. "Electromagnetics from a quasistatic perspective." American Journal of Physics 75.3 (2007): 230-239.
Li, Xiang, et al. "Integrated IVUS-OCT imaging for atherosclerotic plaque characterization." IEEE Journal of Selected Topics in Quantum Electronics 20.2 (2013): 196-203.
Li, Xiang, et al. "Micromachined PIN-PMN-PT crystal composite transducer for high-frequency intravascular ultrasound (IVUS) imaging." IEEE transactions on ultrasonics, ferroelectrics, and frequency control 61.7 (2014): 1171-1178.
Lindner, Jonathan R. "Microbubbles in medical imaging: current applications and future directions." Nature reviews Drug discovery 3.6 (2004): 527-533.
Ma, Jianguo, et al. "A preliminary engineering design of intravascular dual-frequency transducers for contrast-enhanced acoustic angiography and molecular imaging." IEEE transactions on ultrasonics, ferroelectrics, and frequency control 61.5 (2014): 870-880.
Ma, Jianguo, et al. "Design factors of intravascular dual frequency transducers for super-harmonic contrast imaging and acoustic angiography." Physics in Medicine & Biology 60.9 (2015): 3441.
Ma, Jianguo, Michael B. Steer, and Xiaoning Jiang. "An acoustic filter based on layered structure." Applied physics letters 106.11 (2015): 111903.
Ma, Teng, et al. "A review of intravascular ultrasound-based multimodal intravascular imaging: the synergistic approach to characterizing vulnerable plaques." Ultrasonic imaging 38.5 (2016): 314-331.
Madamanchi, Nageswara R., Aleksandr Vendrov, and Marschall S. Runge. "Oxidative stress and vascular disease." Arteriosclerosis, thrombosis, and vascular biology 25.1 (2005): 29-38.
Marcu, Laura, et al. "Discrimination of human coronary artery atherosclerotic lipid-rich lesions by time-resolved laser-induced fluorescence spectroscopy." Arteriosclerosis, thrombosis, and vascular biology 21.7 (2001): 1244-1250.
Packard, René R. Sevag, et al. "Two-point stretchable electrode array for endoluminal electrochemical impedance spectroscopy measurements of lipid-laden atherosclerotic plaques." Annals of biomedical engineering 44.9 (2016): 2695-2706.
Pijls, Nico HJ, et al. "Measurement of fractional flow reserve to assess the functional severity of coronary-artery stenoses." New England Journal of Medicine 334.26 (1996): 1703-1708.
Puri, Rishi, Matthew I. Worthley, and Stephen J. Nicholls. "Intravascular imaging of vulnerable coronary plaque: current and future concepts." Nature Reviews Cardiology 8.3 (2011): 131.
Rudd, James HF, et al. "Imaging atherosclerotic plaque inflammation with [18F]-fluorodeoxyglucose positron emission tomography." Circulation 105.23 (2002): 2708-2711.

(56) References Cited

OTHER PUBLICATIONS

Stefanadis, Christodoulos, et al. "Thermal heterogeneity within human atherosclerotic coronary arteries detected in vivo: a new method of detection by application of a special thermography catheter." Circulation 99.15 (1999): 1965-1971.

Vallabhajosula, Shankar, and Valentin Fuster. "Atherosclerosis: imaging techniques and the evolving role of nuclear medicine." Journal of Nuclear Medicine 38.11 (1997): 1788-1796.

Virmani, Renu, et al. "Pathology of the unstable plaque." Progress in cardiovascular diseases 44.5 (2002): 349-356.

Virmani, Renu, et al. "Pathology of the vulnerable plaque." Journal of the American College of Cardiology 47.8S (2006): C13-C18.

Virmani, Renu, et al. "Vulnerable plaque: the pathology of unstable coronary lesions." Journal of interventional cardiology 15.6 (2002): 439-446.

Wang, Bo, et al. "Detection of lipid in atherosclerotic vessels using ultrasound-guided spectroscopic intravascular photoacoustic imaging." Optics express 18.5 (2010): 4889-4897.

Wang, Bo, et al. "Intravascular photoacoustic imaging." IEEE Journal of selected topics in Quantum Electronics 16.3 (2010): 588-599.

Wang, Lihong V. "Multiscale photoacoustic microscopy and computed tomography." Nature photonics 3.9 (2009): 503-509.

Wang, Lihong V., and Song Hu. "Photoacoustic tomography: in vivo imaging from organelles to organs." science 335.6075 (2012): 1458-1462.

Watkins, Stuart, et al. "Clinical Perspective." Circulation 120.22 (2009): 2207-2213.

Weissleder, Ralph, et al. "In vivo imaging of tumors with protease-activated near-infrared fluorescent probes." Nature biotechnology 17.4 (1999): 375-378.

Worthley, Stephen G., et al. "A novel nonobstructive intravascular MRI coil: in vivo imaging of experimental atherosclerosis." Arteriosclerosis, thrombosis, and vascular biology 23.2 (2003): 346-350.

Xu, Minghua, and Lihong V. Wang. "Photoacoustic imaging in biomedicine." Review of scientific instruments 77.4 (2006): 041101.

Yu, Fei, et al. "Electrochemical impedance spectroscopy to characterize inflammatory atherosclerotic plaques." Biosensors and Bioelectronics 30.1 (2011): 165-173.

Yu, Fei, et al. "Elevated electrochemical impedance in the endoluminal regions with high shear stress: Implication for assessing lipid-rich atherosclerotic lesions." Biosensors and Bioelectronics 43 (2013): 237-244.

Yu, Fei, et al. "Electrochemical impedance spectroscopy to assess vascular oxidative stress." Annals of biomedical engineering 39.1 (2011): 287-296.

Anitschkow, Nikolai, and S. Chalatow. "On Experimental Cholesterin Steatosis and Its Significance in the Originof Some Pathological Processes." Arteriosclerosis 3.2 (1983): 178-182.

Kolodgie, Frank D., et al. "The thin-cap fibroatheroma: a type of vulnerable plaque: the major precursor lesion to acute coronary syndromes." Current opinion in cardiology 16.5 (2001): 285-292.

Lindner, Jonathan R., et al. "Microvascular rheology of Definity microbubbles after intra-arterial and intravenous administration." Journal of the American Society of Echocardiography 15.5 (2002): 396-403.

Rouhanizadeh, Mahsa, et al. "Applying indium oxide nanowires as sensitive and selective redox protein sensors." Micro Electro Mechanical Systems, 2004. 17th IEEE International Conference on. (MEMS). IEEE, 2004.

\* cited by examiner

| Histopathology \ Modalities | OCT | IVUS | NIRF | 18FGD-PET | EIS | IVUS-EIS |
|---|---|---|---|---|---|---|
| Thin-cap fibroatheroma | X | X | | | | X |
| Fibrous structure | | X | | | | X |
| Calcification | | X | | | X | X |
| Oxidize LDL/foam cells | | | | | X | X |
| Protease activity | | | X | | | |
| Glucose analogue | | | | X | | |

OCT: optical coherence tomography; IVUS: intravascular ultrasound; NIRF: near infrared fluorescence; 18FGD-PET: 18F-fluorodexyglucose positron emission tomography; IVUS-EIS: an integrated EIS probe guided by high frequency intravascular ultrasound.

|  | Blood* (From Fig.4g) | Blood (From Fig.4h) | Aorta | Plaque | Perivascular fat |
|---|---|---|---|---|---|
| $R_1$ (ohm) | 0.1 | 50 | 0.7 | 1.25e3 | 258 |
| $R_2$ (ohm) | 1682 | 2.42e4 | 1.79e4 | 2.95e4 | 8.49e4 |
| $C$ (F) | 138e-12 | 29.7e-12 | 0.35e-12 | 10.0e-12 | 82.5e-12 |

21B

|  | Blood | Aorta | Plaque⁺ | Perivascular fat⁺ |
|---|---|---|---|---|
| $a$ (mm) | 1 | 0.6 | 0.2 | 0.1 |
| $d$ (mm) | 3 | 3 | 3 | 3 |
| $l$ (mm) | $4\pi \times 1.2/9$ | $4\pi \times 1.9/9$ | $2\pi \times 1.6/3$ | $2\pi \times 2.2/3$ |
| $\sigma^*$ (S/m) | 0.70 | 0.31 | 0.043 | 0.043 |
| $\varepsilon^*$ | 5250 | 7690 | 912 | 912 |

21C

|  | $A$ | $B$ | $A'$ | $B'$ |
|---|---|---|---|---|
| Blood | 1.6820e+3 | 3.9042 | 7.9786e+2 | 0.5098 |
| Aorta | 1.7940e+4 | 1.1232 | 4.7088e+3 | 9.8465 |
| Plaque | 2.9500e+4 | 87.3246 | 1.2988e+5 | 234.529 |
| Peripheral fat | 8.4470e+4 | 5.9174e+3 | 3.5718e+5 | 6.4544e+2 |

Figure 21A – Figure 21C

ELECTROCHEMICAL IMPEDANCE SPECTROSCOPY

CROSS-REFERENCE TO RELATED APPLICATIONS

This application is a national stage entry of PCT Application No. PCT/US17/31779, filed May 9, 2017, which claims priority to U.S. Provisional Patent Application No. 62/333,608, filed May 9, 2016, and to U.S. Provisional Patent Application No. 62/490,310, filed Apr. 26, 2017, the contents of all of which are incorporated by reference herein in their entirety.

STATEMENT REGARDING FEDERALLY SPONSORED RESEARCH OR DEVELOPMENT

This invention was made with Government support under grant numbers HL083015, HL111437, HL118650, HL129727, awarded by the National Institutes of Health. The Government has certain rights in the invention. This work was supported by the U.S. Department of Veterans Affairs, and the Federal Government has certain rights in the invention.

BACKGROUND OF THE INVENTION

Plaque rupture is the primary mechanism underlying acute coronary syndromes and stroke (Bamford J et al., The Lancet 337.8756 (1991): 1521-1526; Davies P F et al., Proceedings of the National Academy of Sciences 83.7 (1986): 2114-2117; Madamanchi N et al., Arteriosclerosis, thrombosis, and vascular biology 25.1 (2005): 29-38; Virmani R et al., Progress in cardiovascular diseases 44.5 (2002): 349-356; Virmani R et al., Journal of interventional cardiology 15.6 (2002): 439-446). Despite the advent of computed tomographic (CT) angiography, high resolution MRI (Worthley S G et al., Arteriosclerosis, thrombosis, and vascular biology 23.2 (2003): 346-350), intravascular ultrasound (IVUS) (Fayad Z A et al., Circulation research 89.4 (2001): 305-316; Vallabhajosula S et al., The Journal of Nuclear Medicine 38.11 (1997): 1788), near-infrared fluorescence (Jaffer F A et al., Circulation 118.18 (2008): 1802-1809), and time-resolved laser-induced fluorescence spectroscopy (Marcu L et al., Arteriosclerosis, thrombosis, and vascular biology 21.7 (2001): 1244-1250), real-time detection of the atherosclerotic lesions prone to rupture remains an unmet clinical challenge (Finn A V et al., Arteriosclerosis, thrombosis, and vascular biology 30.7 (2010): 1282-1292; Kim D H et al., science 333.6044 (2011): 838-843).

There is a need in the art for improved devices and methods for real-time detection and characterization of atherosclerotic lesions. The present invention meets this need.

SUMMARY OF THE INVENTION

The present invention relates to a tissue characterizing device comprising: a first catheter comprising a lumen, a closed distal end, and an open proximal end; a second catheter comprising a lumen, a distal end, and an open proximal end; at least one ultrasound transducer positioned in the first catheter lumen near the closed distal end; an expandable element near the distal end of the second catheter; and a sensor positioned on the expandable element.

In one embodiment, the first catheter lumen and the second catheter lumen are adjacent and parallel to each other. In one embodiment, the first catheter and the second catheter are co-axial, wherein the first catheter is at least partially enveloped in the lumen of the second catheter. In one embodiment, the distal end of the second catheter forms a seal with the first catheter such that a length of the first catheter extends past the distal end of the second catheter. In one embodiment, the lumen of the first catheter is filled with a fluid. In one embodiment, the at least one ultrasound transducer is attached to a distal end of a torque wire. In one embodiment, the at least one ultrasound transducer is rotatable within the lumen of the first catheter. In one embodiment, the expandable element is a balloon. In one embodiment, the sensor is an electrochemical impedance spectroscopy (EIS) sensor. In one embodiment, the EIS sensor comprises a two-point electrode.

In one embodiment, the first catheter comprises an inner diameter between about 0.5 and 2 mm. In one embodiment, the second catheter comprises an inner diameter between about 1 and 3 mm. In one embodiment, the balloon can be inflated to a diameter between about 1 and 15 mm. In one embodiment, the balloon lies flush with the diameter of the second catheter when deflated. In one embodiment, the device further comprises at least one pressure sensor, at least one temperature sensor, at least one flow sensor, or any combination thereof.

In another aspect, the invention relates to a method of characterizing a tissue region of interest, comprising the steps: positioning the device of the present invention near a tissue; imaging the tissue with an ultrasound transducer on the device to locate a region of interest; positioning the device such that a sensor on the device faces the region of interest; touching the sensor of the device to the region of interest by expanding an expandable element on the device; and characterizing the region of interest with the sensor.

In one embodiment, the sensor is an EIS sensor. In one embodiment, the EIS sensor measures impedance by driving an AC current through the region of interest. In one embodiment, the AC current is driven with a voltage between about 10 and 100 mV. In one embodiment, an impedance spectrum is obtained by measuring current over a frequency sweep between about 100 Hz and 5 MHz.

In one embodiment, the region of interest is an atheroma. In one embodiment, high impedance of an atheroma indicates a high level of oxidized low density lipoprotein (oxLDL) and macrophage/foam cells present in the atheroma. In one embodiment, high impedance of an atheroma is indicative of a high risk of atheroma rupture.

In another aspect, the present invention relates to a tissue characterizing device comprising: a catheter comprising a lumen, a closed distal end, an open proximal end, and at least one aperture near the distal end; a balloon positioned near the distal end of the catheter fluidly connected to the lumen of the catheter by the at least one aperture; and a plurality of sensors positioned on the exterior of the balloon.

In one embodiment, the plurality of sensors comprises electrochemical impedance spectroscopy (EIS) sensors. In one embodiment, each of the EIS sensors comprises a strip of conductive material set on a flexible substrate. In one embodiment, the strip of conductive material has a length and a width, each between about 0.1 and 1 mm.

In one embodiment, the device comprises at least two groups of three sensors per group, each group of sensors arranged in a row equidistantly about the circumference of the balloon. In one embodiment, a row of sensors is spaced from an adjacent row of sensors by a distance of between about 1 and 5 mm.

In one embodiment, the catheter has an outer diameter between about 0.5 and 1.5 mm. In one embodiment, the balloon lies flush against the catheter when deflated. In one embodiment, the balloon is inflatable using a gas or a liquid. In one embodiment, the balloon has an inflated diameter of between about 2 and 20 mm.

In one embodiment, the device further comprises at least one radio-opaque marker positioned on the catheter.

In another aspect, the present invention relates to a method of characterizing a tissue region of interest, comprising the steps of: positioning a tissue characterizing device near a tissue, the device having a balloon with a plurality of sensors positioned on the surface of the balloon; inflating the balloon to contact at least two of the sensors to the tissue; measuring the impedance between a pair of adjacent sensors contacting the tissue for every permutation of nonrepeating pairs of adjacent sensors contacting the tissue; and generating a 3D impedimetric map of the tissue from the impedance measurements to characterize the tissue.

In one embodiment, the plurality of sensors comprises electrochemical impedance spectroscopy (EIS) sensors. In one embodiment, a device having six sensors contacting a tissue performs at least fifteen impedance measurements, wherein the at least fifteen impedance measurements represent at least one measurement for each of the fifteen permutations of nonrepeating adjacent sensor pairs.

In one embodiment, the impedance between a pair of adjacent sensors is measured by driving an AC current between the pair of adjacent sensors. In one embodiment, the AC current is driven with a voltage between about 1 and 100 mV. In one embodiment, an impedance spectrum between a pair of adjacent sensors is obtained by measuring current over a frequency sweep between about 1 Hz to 10 MHz.

In one embodiment, the tissue is an artery. In one embodiment, high impedance of a region of artery indicates the presence of a metabolically active atherosclerotic lesion.

In one embodiment, the positioning of the tissue characterizing device is monitored by locating at least one radio-opaque marker embedded on the device.

BRIEF DESCRIPTION OF THE DRAWINGS

The following detailed description of embodiments of the invention will be better understood when read in conjunction with the appended drawings. It should be understood, however, that the invention is not limited to the precise arrangements and instrumentalities of the embodiments shown in the drawings.

FIG. 1A depicts the exemplary sensor in an uninflated state. FIG. 1B depicts the exemplary sensor in an inflated state.

FIG. 4A depicts a side view cross section of the exemplary 3D EIS balloon sensor in an uninflated state. FIG. 4B depicts the exemplary 3D EIS sensor in an inflated state.

(FIG. 5A) Photographs reveal the device prototype with zoomed-in views of balloon-inflation, providing details of the individual electrodes, balloon, and radio-opaque markers. (FIG. 5B) Top and (FIG. 5C) side views provide the dimensions of the 6-point sensor upon balloon-inflation. (FIG. 5D) A 3-dimensional schematic illustration of the 6-point electrochemical impedance spectroscopy (EIS) device highlights the endoluminal deployment strategy upon balloon-inflation (Ø 3 mm). The inset shows the device under the balloon-deflated state (Ø 1 mm) prior to deployment. The individual electrodes (six in total) are in contact with the endoluminal surface upon balloon-inflation.

FIG. 6A depicts the deposition of copper layer and patterning of dry-film photoresist. FIG. 6B illustrates the etching of the copper layer. FIG. 6C depicts the deposition of another polyimide layer and the exposing of sensor electrodes and the contact pad. FIG. 6D illustrates the plating of the Au/Ni layer. FIG. 6E is a schematic of the final device assembly.

(FIG. 10A) The photograph of an exemplary integrated sensor highlights the relative position of the EIS sensor and the ultrasonic transducer. (FIG. 10B) A magnified view of an exemplary EIS sensor illustrates the polyimide substrate for flexibility. (FIG. 10C) A magnified view of an exemplary IVUS transducer inside the inner catheter and its frequency responses.

(FIG. 11A) Without the guidance, the EIS measurements at Site 1 missed the lesions (red arrow). (FIG. 11B) With the IVUS guidance, EIS measurement sites were aligned with Sites 1, 2, and 3. FIG. 11C and FIG. 11D illustrate EIS measurement in terms of impedance magnitude; FIG. 11E and FIG. 11F illustrate EIS measurement in terms of the phase spectra. (FIG. 11C) Frequency-dependent impedance (kΩ) increased between about 100 Hz to 300 kHz in the oxLDL-laden aorta (red, green, and blue) versus the lesion-free aorta (control, black). (FIG. 11D) With the IVUS guidance, the frequency-dependent impedance (red, green, and blue arrows) significantly increased between about 100 Hz to 300 kHz as compared to the control (black). (FIG. 11E) The phase spectrum was indistinct in the random measurements from 100 Hz to 300 kHz. (FIG. 11F) With the guidance, the phase was distinct from the control at <15 kHz.

FIG. 13 is a table comparing individual versus integrated intravascular modalities.

FIG. 15G depicts 3-D mapping of a reconstructed aortic segment with atherosclerosis highlights the 15 (3+6+6) distinct permutations of the EIS impedance measurements with corresponding color scale.

FIG. 21A through FIG. 21C are tables listing (FIG. 21A) the fitting results of the circuit model of FIG. 14G (* only the fitting results for blood obtained from model circuit in FIG. 7G is used); (FIG. 21B) the electrical properties and geometrical variables of different tissue used in the calculation (* conductivity and relative permittivity values obtained from Hasgall P A et al., "IT'IS Database for thermal and electromagnetic parameters of biological tissues. Version 2.6, Jan. 13, 2015." (2015)) († conductivity and relative permittivity of fat are used); and (FIG. 21C) the comparison of impedance values.

DETAILED DESCRIPTION

Figure 1A:
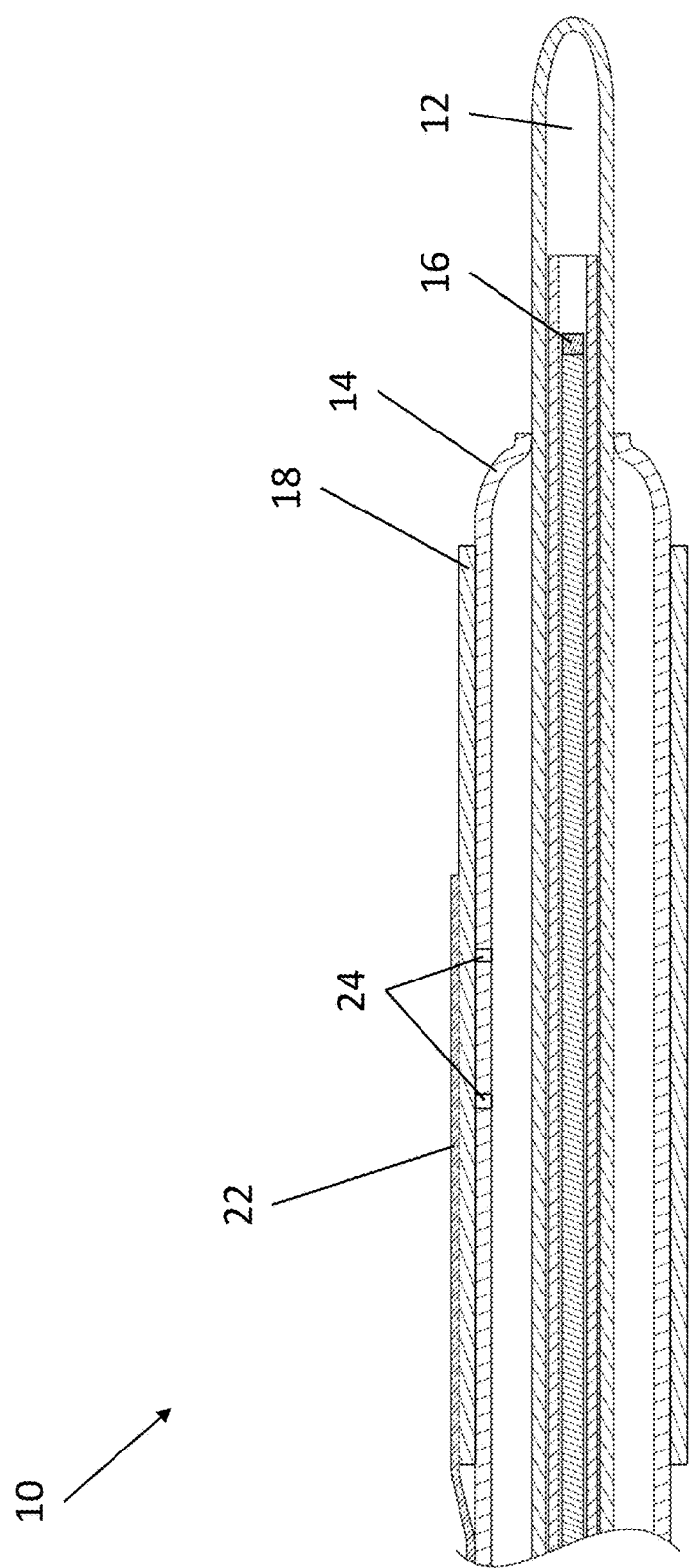
FIG. 1A and FIG. 1B are side view cross sections of an exemplary integrated sensor consisting of an EIS sensor and an IVUS transducer.
Figure 1B:
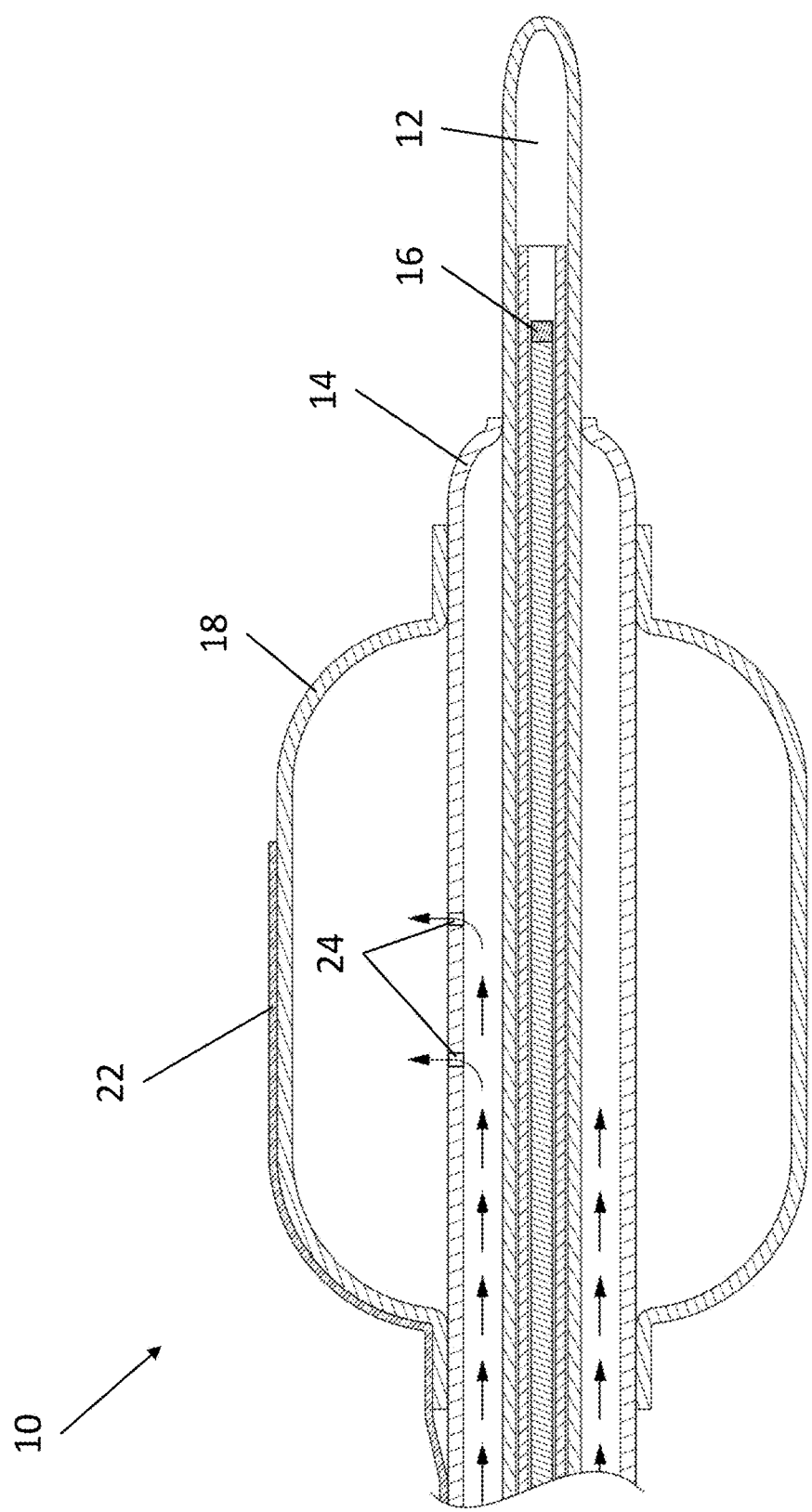

The present invention provides devices for characterizing regions of tissue and methods for using the devices. The devices are capable of locating, identifying, and characterizing tissue regions of interest in vivo. In one embodiment, the devices are ultrasound-guided. In one embodiment, the devices characterize regions of tissue using electrical impedance spectroscopy (EIS) sensors. In one aspect, the devices are useful in predicting plaque rupture, such as by determining the level of oxidized low density lipoprotein (oxLDL) and macrophage/foam cells present in an atheroma. In one aspect, the devices are useful in identifying metabolically active atherosclerotic lesions that are angiographically invisible.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

As used herein, "imaging" may include ultrasonic imaging, be it one dimensional, two dimensional, three dimensional, or real-time three dimensional imaging (4D). Two dimensional images may be generated by one dimensional transducer arrays (e.g., linear arrays or arrays having a single row of elements). Three dimensional images may be produced by two dimensional arrays (e.g., those arrays with elements arranged in an n by n planar configuration) or by mechanically reciprocated, one dimensional transducer arrays.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, "sonolucent" is defined as a property wherein a material is capable of transmitting ultrasound pulses without introducing significant interference, such that an acceptable acoustic response can be obtained from the body structure(s) of interest.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Ultrasound-Guided Electrochemical Impedance Spectroscopy Device

In one aspect, the present invention relates to devices for characterizing regions of tissue. Referring now to FIG. 1A, FIG. 1B, FIG. 2A, and FIG. 2B, a device 10 is depicted. Device 10 comprises a first catheter 12 and a second catheter 14. First catheter 12 comprises a lumen having an open proximal end and a closed distal end. First catheter 12 can have any suitable length, such as a length between about 10 and 200 cm. In some embodiments, first catheter 12 comprises an inner diameter between about 0.5 and 2 mm. The inner diameter of first catheter 12 is preferably sized to fit ultrasound transducer 16. Ultrasound transducer 16 can be any suitable transducer in the art, such as a piezoelectric ultrasound transducer or a capacitive ultrasound transducer. In various embodiments, device 10 can comprise one, two, three, four, or more ultrasound transducers 16. Ultrasound transducer 16 is preferably positioned at the closed distal end of first catheter 12. In some embodiments, ultrasound transducer 16 may be freely rotated within the lumen of first catheter 12, such as by attachment to a torque wire. In some embodiments, ultrasound transducer 16 is immersed in a fluid within first catheter 12. For example, first catheter 12 may be filled with water or phosphate buffered saline to maintain at least partial consistency in ultrasound signal propagation.

Second catheter 14 comprises a lumen an open proximal end and a distal end. In some embodiments, second catheter 14 is parallel and adjacent to first catheter 12, wherein the distal end of second catheter 14 is closed. In some embodiments, second catheter 14 at least partially envelopes first catheter 12, wherein second catheter 14 and first catheter 12 are co-axial. In one embodiment, the distal end of second catheter 14 is closed around the outer surface of a co-axial first catheter 12, such that the distal end of outer catheter 14 forms a seal around first catheter 12. In some embodiments, the seal fuses second catheter 14 to first catheter 12. In other embodiments, the seal permits independent rotation between second catheter 14 and first catheter 12. Second catheter 14 can have any suitable length, such as between about 10 and 200 cm. In some embodiments, second catheter 14 comprises an inner diameter between about 1 and 3 mm.

Positioned near the distal end of outer catheter is sensor 22 for characterizing a region of tissue. In one embodiment, sensor 22 is an EIS sensor. An EIS sensor can have any suitable sensor design, such as those recited in U.S. patent application Ser. No. 14/981,089, the contents of which are incorporated herein in its entirety. In some embodiments, the EIS sensor has a two-point electrode design, wherein two strips of conductive material are arranged in parallel with a gap in between. Exemplary dimensions include electrode lengths between about 0.2 and 5 mm, electrode widths between about 0.1 and 5 mm, and gap distances between about 0.1 and 5 mm. In some embodiments, the electrodes of an EIS sensor are set in a flexible substrate.

For the purposes of bringing sensor 22 into physical contact with a region of tissue for characterization, the distal end of second catheter 14 has an expandable element for attaching sensor 22. For example, in some embodiments, the expandable element can be an extendable arm or membrane. By attaching to the expandable element, sensor 22 can be brought closer to a region of interest. For example, to examine a region of the inner surface of a blood vessel, balloon 18 may be inflated such that the exterior of balloon 18 presses EIS sensor 22 against the region. In other embodiments, the expandable element can be a balloon 18, which can be inflatable and deflatable via at least one aperture 24 on second catheter 14. Balloon 18 preferably comprises an elastic material, such that balloon 18 expands when inflated and shrinks when deflated. Balloon 18 can have any suitable diameter when inflated, such as a diameter between about 1 and 15 mm. Preferably, the expandable element lies close to or is flush with the outer surface of second catheter 14 when not expanded.

In certain embodiments, device 10 can include additional sensors, such as pressure sensors, flow sensors, temperature sensors, and the like. For example, in one embodiment, device 10 can comprise at least two sensors, wherein a first distal sensor can provide distal measurements, and a proximal measure can provide proximal measurements. The at least two sensors may be positioned upstream and downstream from a region of interest, such as in a fractional flow reserve technique.

In some embodiments, the devices of the present invention may operate in conjunction with a computer platform system, such as a local or remote executable software platform, or as a hosted internet or network program or portal. In certain embodiments, portions of the system may be computer operated, or in other embodiments, the entire system may be computer operated. As contemplated herein, any computing device as would be understood by those skilled in the art may be used with the system, including desktop or mobile devices, laptops, desktops, tablets, smartphones or other wireless digital/cellular phones, televisions or other thin client devices as would be understood by those skilled in the art.

The computer platform is fully capable of sending and interpreting device emissions signals as described herein throughout. For example, the computer platform can be configured to control ultrasound and EIS sensor parameters such as frequency, intensity, amplitude, period, wavelength, pulsing, and the like. The computer platform can also be configured to monitor and record insertion depth and location. The computer platform can be configured to record received signals, and subsequently interpret the signals. For example, the computer platform may be configured to interpret ultrasound signals as images and subsequently transmit the images to a digital display. The computer platform may also be configured to interpret changes in impedance and subsequently transmit the recorded changes to a digital display. The computer platform may further perform automated calculations based on the received signals to output data such as density, distance, composition, imaging, and the like, depending on the type of signals received. The computer platform may further provide a means to communicate the received signals and data outputs, such as by projecting one or more static and moving images on a screen, emitting one or more auditory signals, presenting one or more digital readouts, providing one or more light indicators, providing one or more tactile responses (such as vibrations), and the like. In some embodiments, the computer platform communicates received signals and data outputs in real time, such that an operator may adjust the use of the device in response to the real time communication. For example, in response to a stronger received signal, the computer platform may output a more intense light indicator, a louder auditory signal, or a more vigorous tactile response to an operator.

The devices of the present invention can be made using any suitable method known in the art. The method of making may vary depending on the materials used. For example, devices substantially comprising a plastic or polymer may be milled from a larger block or injection molded. Likewise, devices substantially comprising a metal may be milled, cast, etched, or deposited by techniques such as chemical vapor deposition, spraying, sputtering, and ion plating. In some embodiments, the devices may be made using 3D printing techniques commonly used in the art.

In various embodiments, the components of the present invention, including first catheter 12, second catheter 14, expandable element such as balloon 18, and sensor 22, are constructed from a biocompatible material. Preferably, the material is flexible, such that device 10 is at least partially pliable for improved range and reach. In certain embodiments, the components of the present invention are at least partially sonolucent.

Figure 3:
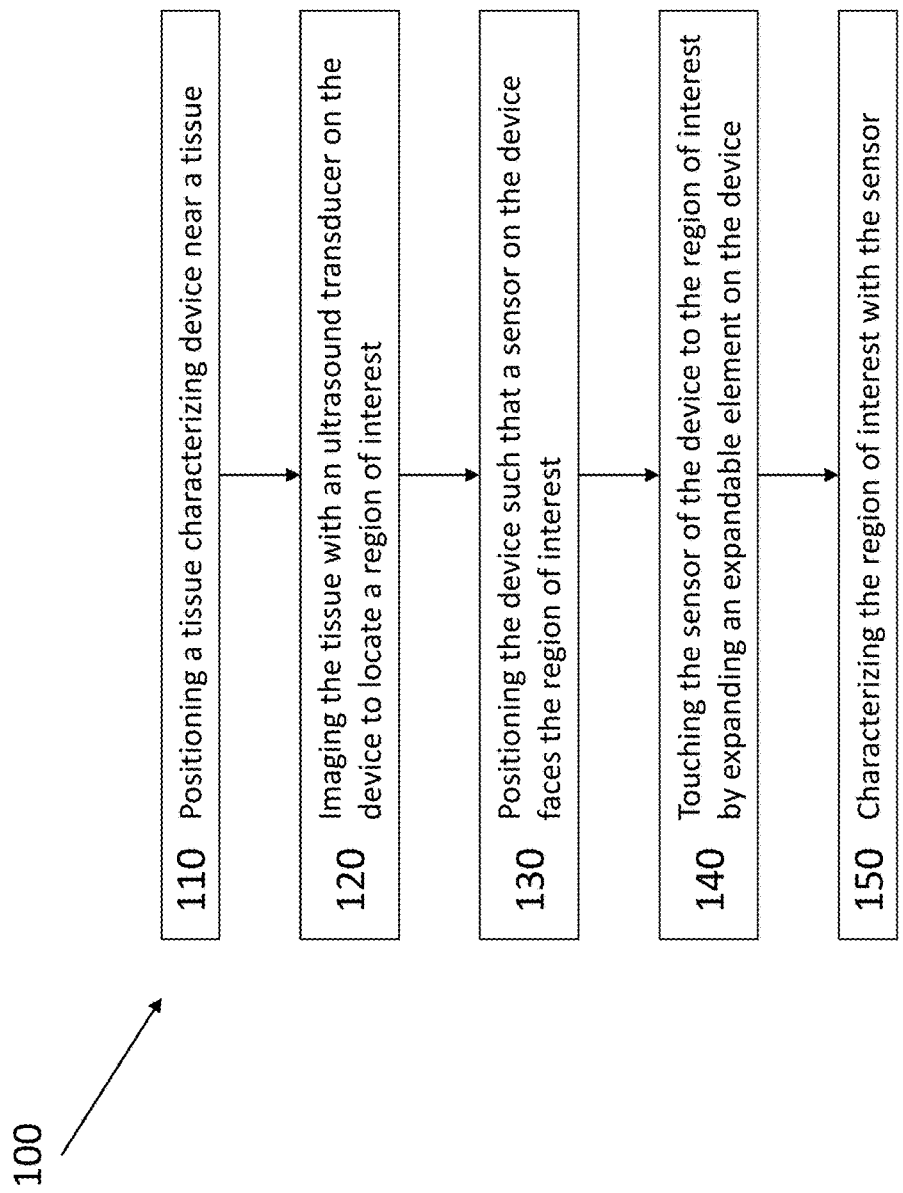
FIG. 3 is a flowchart depicting an exemplary method of using an ultrasound-guided EIS device to characterize a tissue region of interest.
Figure 4A:
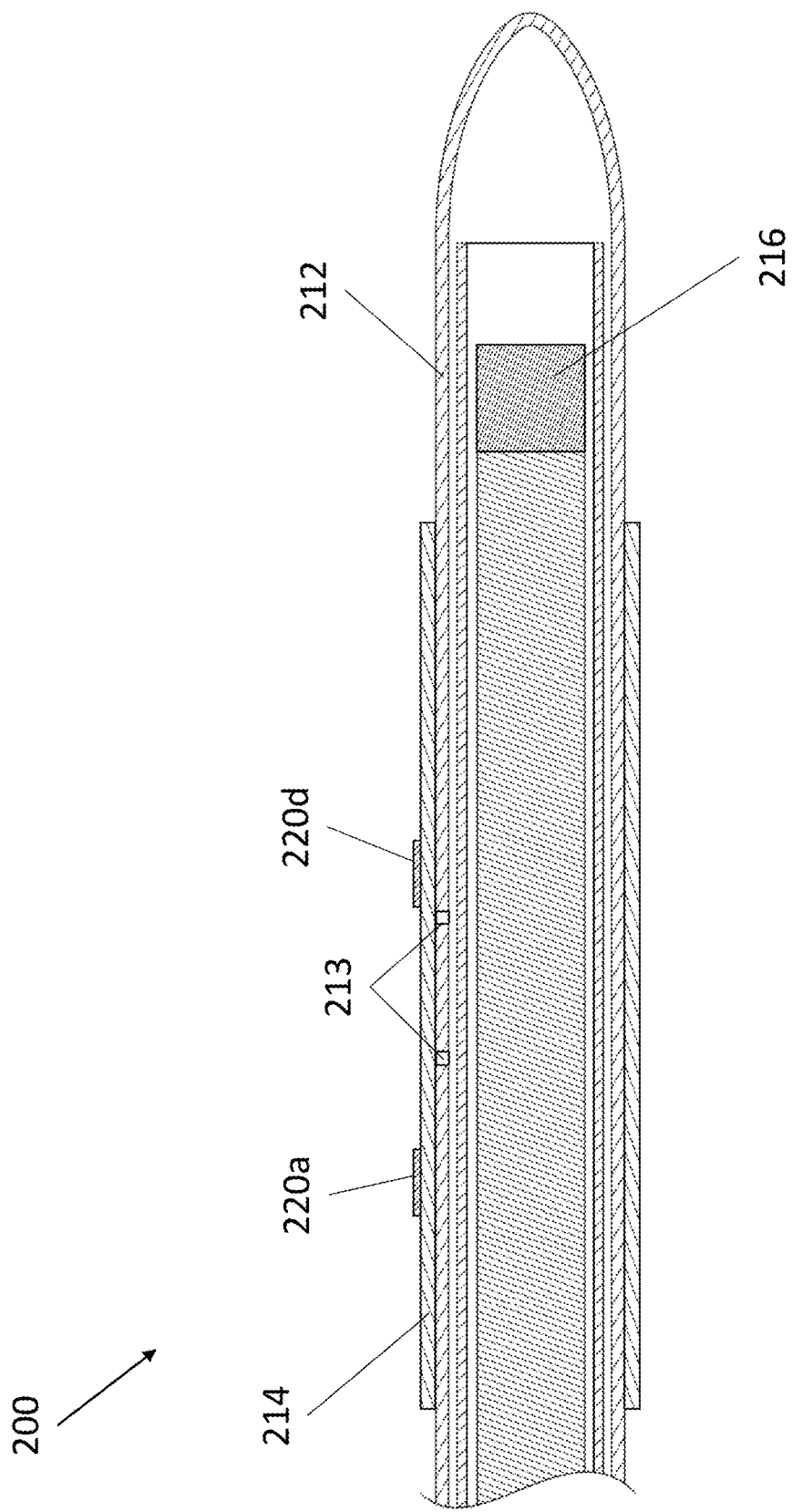
FIG. 4A and FIG. 4B depict an exemplary 3D EIS balloon sensor.
Figure 4B:
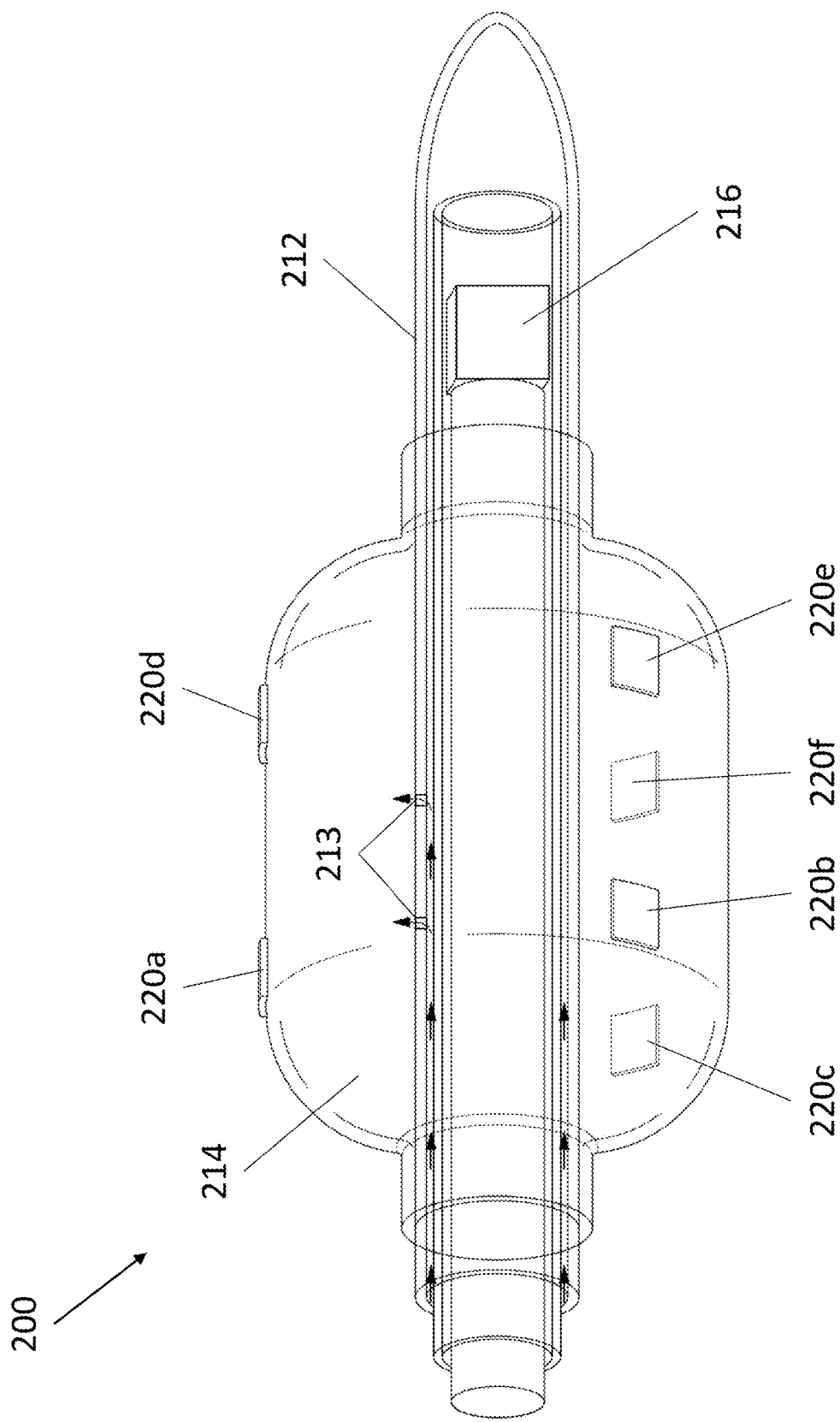

In another aspect, the present invention provides method for using the ultrasound-guided electrochemical impedance spectroscopy devices of the present invention, such as in tissue imaging and characterization of regions of interest. Referring now to FIG. 3, an exemplary method 100 of accurately characterizing a tissue region of interest is presented. Method 100 begins with step 110, wherein an exemplary device of the present invention is positioned near a tissue. In step 120, the tissue is imaged with an ultrasound transducer on the device to locate a region of interest. In step 130, the ultrasound imaging data is used to position the device such that a sensor on the device faces the region of interest. In step 140, the sensor of the device is touched to the region of interest by expanding an expandable element on the device. In step 150, the region of interest is characterized using the sensor.

As described elsewhere herein, the devices of the present invention include embodiments using ultrasound guidance and EIS sensors to locate, identify, and characterize tissue in vivo. The devices and methods are useful in many applications, such as diagnosing tissue abnormalities or lesions in difficult to reach areas. For example, the devices and methods may be used to locate plaques in an artery and determine the likelihood of rupture based on plaque content.

With reference to FIG. 3, characterizing a plaque may begin with placing an ultrasound-guided EIS device of the present invention in a patient's artery, wherein ultrasound imaging can determine the location, orientation, and size of any plaques present. Based on the ultrasound imaging data, an operator may position the device such that the EIS sensor faces a particular region of a plaque to characterize. The balloon is then inflated to touch the EIS sensor to the region of interest. The balloon can be inflated with air or fluid, and pressure can vary depending on the size of the balloon and the size of the artery.

Once the EIS sensor has been brought into physical contact with the region of interest, impedance is determined by driving an AC current through the plaque using the EIS sensor. Any suitable voltage may be used, such as voltages between about 10 and 100 mV. To obtain an impedance spectrum, current is measured by swiping the frequencies, such as in a range anywhere between about 100 Hz to 5 MHz. A determination of plaque stability may be made based on the impedance values, wherein higher impedance spectra indicate higher oxLDL and macrophage/foam cell content and a greater chance of rupture.

3D Electrochemical Impedance Spectroscopy Device

The present invention also relates to devices for characterizing 3D regions of tissue. The devices include a 6-point electrode configuration. This configuration enables 15 alternating EIS permutations of 2-point electrode arrays. This configuration allows for comprehensive impedance mapping and detection of lipid-rich atherosclerotic lesions.

Referring now to FIG. 4A, FIG. 4B, and FIG. 5A through FIG. 5D, an exemplary device 210 is depicted. Device 210 comprises catheter 212 and inflatable balloon 214. Catheter 212 comprises a lumen having an open proximal end and a closed distal end. In various embodiments, the distal end of catheter 212 comprises one or more features for locating device 210, such as one or more radio-opaque marker 216 shown in FIG. 5A. Catheter 212 can have any suitable length as determined by one skilled in the art. Catheter 212 can have any suitable diameter, such as a diameter between about 0.5 and 1.5 mm.

Balloon 214 is positioned near the distal end of catheter 212. In various embodiments, catheter 212 comprises at least one aperture 213 such that the lumen of catheter 212 is fluidly connected to the interior of balloon 214, such as for inflation purposes. Balloon 214 can be inflated using any appropriate substance, including air, an inert gas, or an aqueous solution. Balloon 214 can have any suitable dimension as determined by one skilled in the art. For example, in a deflated conformation depicted in FIG. 5D, balloon 214 lies flush against the exterior of catheter 212 and can have a diameter slightly larger than the diameter of catheter 212, accounting for the thickness of balloon 214 material. Typical deflated balloon 214 diameters can be between about 1 and 2 mm. In an inflated conformation shown in FIG. 5D, balloon 214 can have a diameter between about 2 and 20 mm.

Figures 5A, 5B, 5C, 5D:
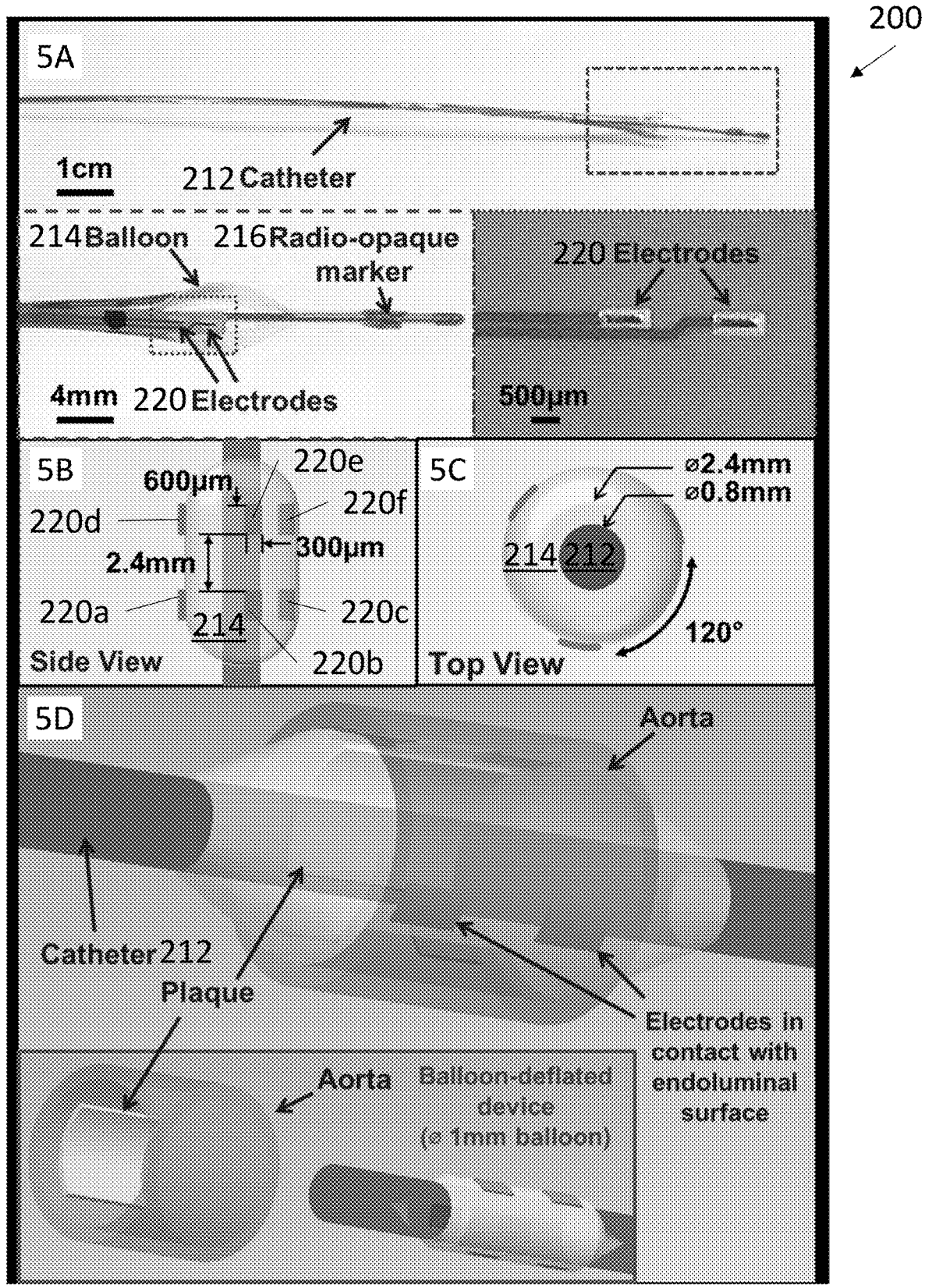
FIG. 5A through FIG. 5D depict the design and deployment of the balloon-inflatable electrodes.

Balloon 214 comprises a plurality of electrodes 220. Electrodes 220 can have any suitable design. For example, electrodes 220 can each comprise a single strip of conductive material set on a flexible substrate. Exemplary dimensions include electrode lengths between about 0.1 and 1 mm, and widths between about 0.1 and 1 mm. In certain embodiments, electrodes 220 are arranged in two circumferential rows. In one embodiment, such as in FIG. 5B and FIG. 5C, balloon 214 comprises six electrodes 220, wherein a first group of three electrodes 220a, 220b, and 220c are arranged equidistantly about the circumference of balloon 214 closer to the proximal end of catheter 212, and a second group of three electrodes 220d, 220e, and 220f are arranged equidistantly about the circumference of balloon 214 closer to the distal end of catheter 212. In various embodiments, the first group and the second group of electrodes can be separated by a distance between about 1 and 5 mm. As will be understood by those having skill in the art, the equidistant arrangement of the three electrodes in the first and second groups provides a 120° separation between adjacent electrodes, as depicted in FIG. 5C.

In various embodiments, device 210 may further comprise one or more features for enhancing the performance of the device. For example, in some embodiments device 210 may further comprise a covering to protect or insulate the components of device 210, such as one or more heat-shrink tubing 222 and 224 depicted in FIG. 6E. In certain embodiments, device 210 can include additional sensors, such as pressure sensors, flow sensors, temperature sensors, and the like.

In some embodiments, device 210 may operate in conjunction with a computer platform system, such as a local or remote executable software platform, or as a hosted internet or network program or portal. In certain embodiments, portions of the system may be computer operated, or in other embodiments, the entire system may be computer operated. As contemplated herein, any computing device as would be understood by those skilled in the art may be used with the system, including desktop or mobile devices, laptops, desktops, tablets, smartphones or other wireless digital/cellular phones, televisions or other thin client devices as would be understood by those skilled in the art.

The computer platform is fully capable of sending and interpreting device emissions signals as described herein throughout. For example, the computer platform can be configured to control EIS sensor parameters such as frequency, intensity, amplitude, period, wavelength, pulsing, and the like. The computer platform can also be configured to monitor and record insertion depth and location. The computer platform can be configured to record received signals, and subsequently interpret the signals. For example, the computer platform may be configured to interpret EIS signals between selected electrodes. The computer platform may also be configured to interpret changes in impedance and subsequently transmit the recorded changes to a digital display. The computer platform may further perform automated calculations based on the received signals to output data such as density, distance, composition, imaging, and the like, depending on the type of signals received. The computer platform may further provide a means to communicate the received signals and data outputs, such as by projecting one or more static and moving images on a screen, emitting one or more auditory signals, presenting one or more digital readouts, providing one or more light indicators, providing one or more tactile responses (such as vibrations), and the like. In some embodiments, the computer platform communicates received signals and data outputs in real time, such that an operator may adjust the use of the device in response to the real time communication. For example, in response to a stronger received signal, the computer platform may output a more intense light indicator, a louder auditory signal, or a more vigorous tactile response to an operator.

The devices of the present invention can be made using any suitable method known in the art. The method of making may vary depending on the materials used. For example, devices substantially comprising a plastic or polymer may be milled from a larger block or injection molded. Likewise, devices substantially comprising a metal may be milled, cast, etched, or deposited by techniques such as chemical vapor deposition, spraying, sputtering, and ion plating. In some embodiments, the devices may be made using 3D printing techniques commonly used in the art.

In various embodiments, the components of the present invention, including catheter 212, balloon 214, radiopaque marker 216, electrodes 220, heat-shrink tubing 222, and heat-shrink tubing 224, are constructed from a biocompatible material. Preferably, the material is flexible, such that device 210 is at least partially pliable for improved range and reach.

Figure 7:
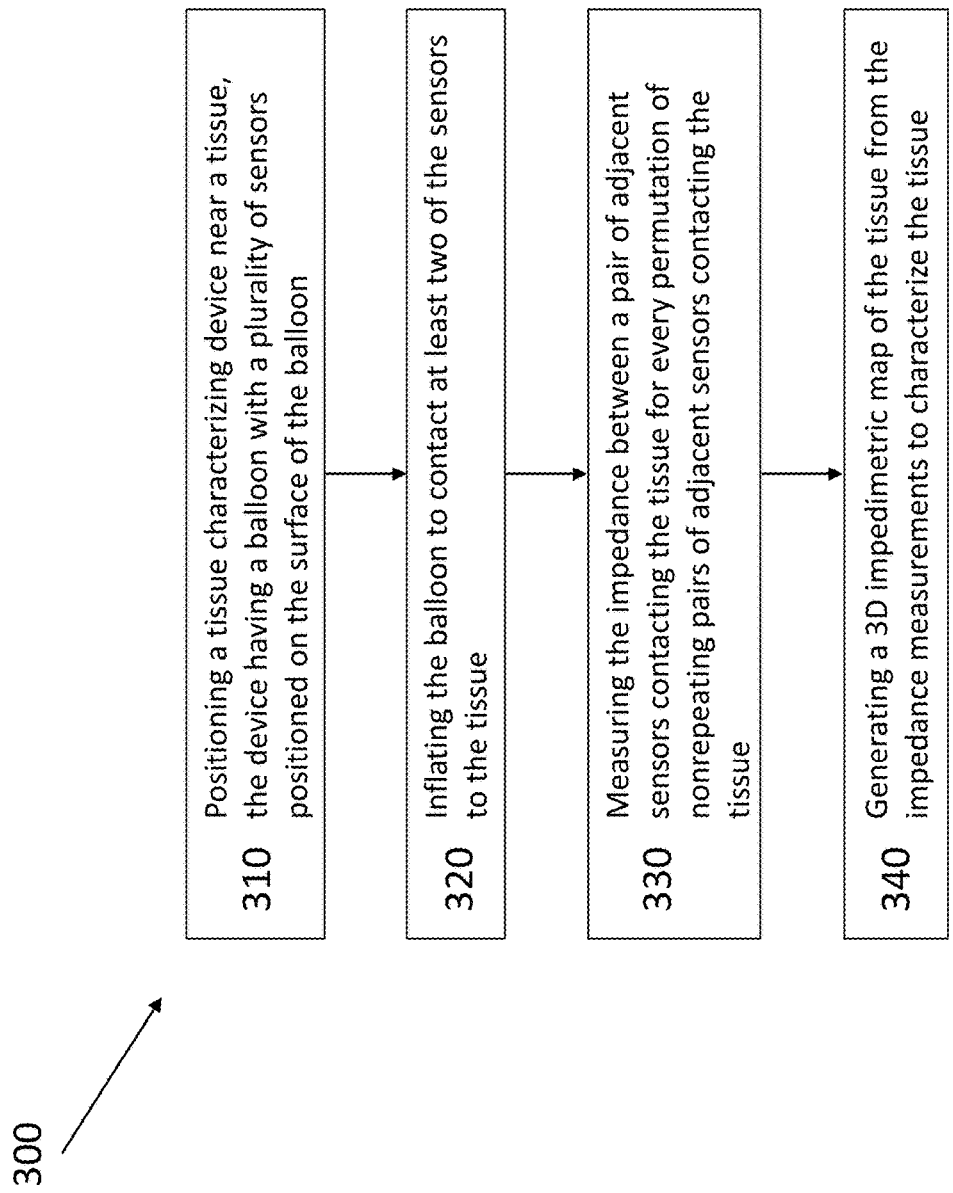
FIG. 7 is a flowchart depicting an exemplary method of using a balloon inflatable EIS device to characterize a tissue region of interest.

In another aspect, the present invention provides method for using the 3D electrochemical impedance spectroscopy devices of the present invention, such as in tissue imaging and characterization of regions of interest. Referring now to FIG. 7, an exemplary method 300 of accurately characterizing a tissue region of interest is presented. Method 300 begins with step 310, wherein an exemplary device of the present invention having a balloon with a plurality of sensors positioned on the surface of the balloon is positioned near a tissue. In step 320, the balloon is inflated to contact at least two of the sensors to the tissue. In step 330, the impedance between a pair of adjacent sensors contacting the tissue is measured, for every permutation of nonrepeating pairs of adjacent sensors contacting the tissue. In step 340, the tissue is characterized by generating a 3D impedimetric map of the tissue from the impedance measurements.

As described elsewhere herein, the devices of the present invention use EIS sensors to characterize tissue in vivo. The devices and methods are useful in many applications, such as diagnosing tissue abnormalities in difficult to reach areas or identifying lesions not visible through conventional imaging. For example, the devices and methods may be used to detect angiographically invisible atherosclerotic lesions that are metabolically active.

With reference to FIG. 7, characterizing a plaque may begin with placing an EIS device of the present invention in a patient's artery, wherein the balloon is inflated to touch the EIS sensors to the inner surface of a section of the artery. The balloon can be inflated with air or fluid, and pressure can vary depending on the size of the balloon and the size of the artery.

Once the EIS sensors have been brought into physical contact with the inner surface of the section of the artery, impedance is measured between every pair of adjacent EIS sensors by driving an AC current through the tissue using the EIS sensors. Any suitable voltage may be used, such as voltages between about 1 and 100 mV. To obtain an impedance spectrum, current is measured by swiping the frequencies, such as in a range anywhere between about 1 Hz to 10 MHz. Combining the EIS measurements from every permutation of nonrepeating adjacent EIS sensor pairs generates a 3D impedimetric map of the section of artery, wherein higher impedance spectra indicate the presence of metabolically active lipids.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art may, using the preceding description and the following illustrative examples, utilize the present invention and practice the claimed methods. The following working examples therefore, specifically point out the preferred embodiments of the present invention, and are not to be construed as limiting in any way the remainder of the disclosure.

Example 1: Plaque Characterization Using Integrated Electrochemical Spectrum and Intravascular Ultrasound Sensors Vulnerable plaque rupture is the leading cause of death in the developed world. Growing evidence suggests that thin-cap fibroatheromas rich in macrophage/foam cells and oxidized low density lipoprotein (oxLDL) are prone to destabilization. However, it is challenging to characterize the vulnerable plaques with individual detection methods. Presented herein is an integrated sensor composed of an electrochemical spectrum (EIS) sensor to measure plaque laden with oxLDL and a broadband intravascular ultrasound (IVUS) transducer to acquire plaque morphology. Correlation analysis of EIS and IVUS results leads to improved characterization of the vulnerable plaques in vivo.

Figures 8A, 8B, 8C:
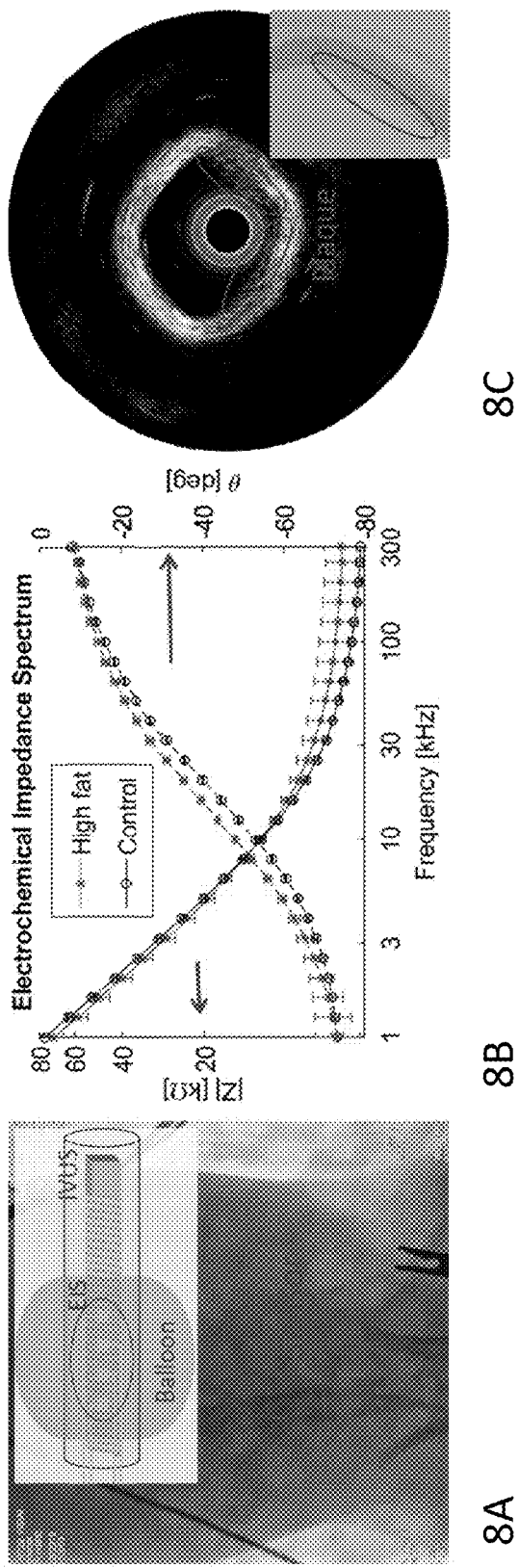
FIG. 8A depicts the structure of an exemplary integrated sensor and an experimental image.
FIG. 8B depicts electrochemical impedance spectroscopy (EIS) values obtained using an exemplary integrated sensor.
FIG. 8C depicts an intravascular ultrasound (IVUS) image of a plaque in a vessel and an immunohistology image of a plaque in a vessel (inset).

The integrated sensor was fabricated on an acoustic-transparent ethylene-vinyl acetate (EVA) tube. The IVUS transducer with a center frequency of 15 MHz was mounted at the tip of a torque coil and fitted inside the tube. The EIS sensor was attached on a balloon mounted on the outer surface of the EVA tube (see FIG. 8A). The chirp signal was used to excite the IVUS transducer and pulse compression algorithm was used to improve the imaging quality. Then the EIS sensor was positioned to areas of plaques and the EIS was acquired with the balloon inflated.

The integrated sensors were deployed in 7 rabbits: 4 control rabbits fed on normal chow and 3 rabbits fed on a high-fat diet to develop atherosclerotic plaques. The EIS results (FIG. 8B) indicate >15% differences on the impedance magnitude at >100 kHz and >11% differences on the phase at 15-100 kHz between the high fat diet and the control group. The IVUS imaging result (FIG. 8C) reveals the plaques inside the lumen, which were validated by histology. In the imaging position, the plaques cover about 40% of the lumen. The prototype iteration of the sensor does not account for the relative orientation of the EIS and IVUS sensors. As a result, the EIS sensor may not be positioned directly on the plaques of interest, leading to a relatively large standard deviation (up to 17%).

Example 2: Ultrasonic Transducer-Guided Electrochemical Impedance Spectroscopy to Lipid-Laden Plaques Previous studies have demonstrated that endoluminal EIS distinguishes pre-atherogenic lesions associated with oxidative stress in fat-fed New Zealand White (NZW) rabbits (Ai L et al., American Journal of Physiology-Cell Physiology 294.6 (2008): C1576-C1585; Hwang J et al., Free Radical Biology and Medicine 41.4 (2006): 568-578; Rouhanizadeh M et al., Micro Electro Mechanical Systems, 2004. 17th IEEE International Conference on. (MEMS). IEEE, 2004; Yu F et al., Biosensors and Bioelectronics 30.1 (2011): 165-173; Yu F et al., Annals of biomedical engineering 39.1 (2011): 287-296). Specifically, vessel walls harboring oxidized low density lipoprotein (oxLDL) exhibit distinct EIS signals (Yu F et al., Annals of biomedical engineering 39.1 (2011): 287-296). oxLDL and foam cell infiltrates in the subendothelial layer engendered an elevated frequency-dependent EIS by using concentric bipolar microelectrodes (Yu F et al., Annals of biomedical engineering 39.1 (2011): 287-296). Specific electric elements were evaluated to simulate working and counter electrodes at the electrode-endoluminal tissue interface (Yu F et al., Biosensors and Bioelectronics 30.1 (2011): 165-173). The application of EIS strategy was established to detect oxLDL-rich fibroatheroma using explants of human coronary, carotid, and femoral arteries (Yu F et al., Biosensors and Bioelectronics 30.1 (2011): 165-173). The regions of elevated EIS correlated with intimal thickening detected via high-frequency (60

MHz) IVUS imaging and by prominent oxLDL staining (Cao H et al., Biosensors and Bioelectronics 54 (2014): 610-616).

In this context, the following study integrates both IVUS imaging and EIS measurements to characterize the metabolically active, albeit non-obstructive lesions when patients are undergoing diagnostic angiogram or primary coronary intervention. Rupture-prone plaques consist of oxLDL and necrotic core with low conductivity. When alternating current (AC) is applied to a plaque, the oxLDL-rich lesion is analogous to a capacitance component, exhibiting both elevated electrical impedance magnitude and negative phase. The divergence of electrical impedance between the oxLDL-laden plaque and healthy vessel provides a sensitive and specific assessment of atherosclerotic lesions. A catheter-based 2-point micro-electrode configuration was developed for intravascular deployment in NZW rabbits (Packard R R S et al., Annals of biomedical engineering 44.9 (2016): 2695-2706). An array of 2 flexible rectangular electrodes, 3 mm in length by 300 µm in width, and separated by 300 µm, was microfabricated and mounted on an inflatable balloon catheter for EIS measurement of oxLDL-rich lesions. Upon balloon inflation by air pressure, the 2-point electrode array conformed to the arterial wall to increase sensitivity by deep intraplaque penetration via alternating current (AC). The frequency sweep from 100 Hz-300 kHz generated distinct changes in both impedance ($\Omega$) and phase ($\phi$) in relation to varying degrees of intraplaque oxLDL burden in the aorta (Packard R R S et al., Annals of biomedical engineering 44.9 (2016): 2695-2706).

Figures 2A, 2B:
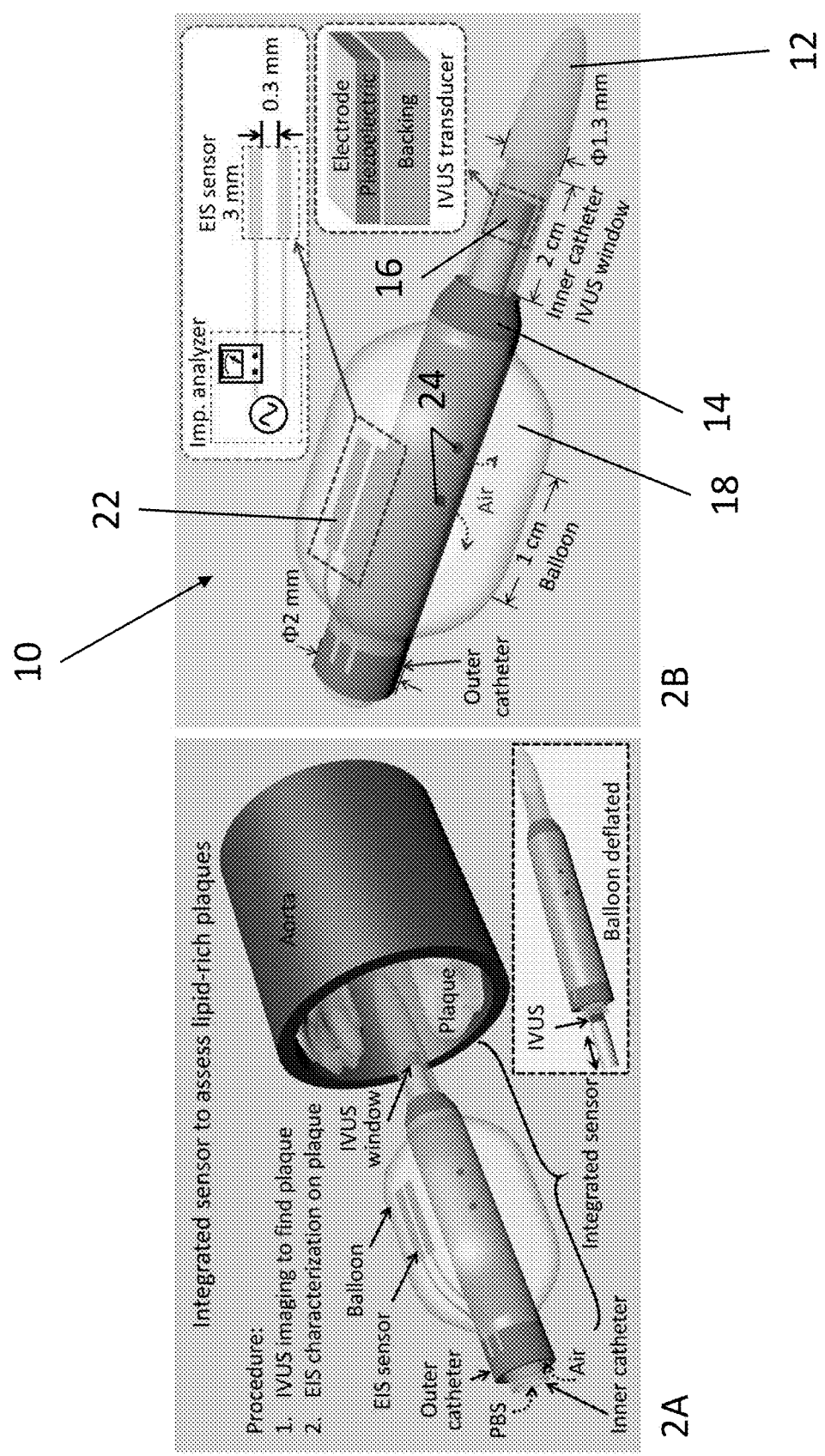
FIG. 2A is a conceptual illustration depicting the deployment of an exemplary integrated sensor consisting of an EIS sensor and an IVUS transducer to assess lipid-rich plaques. The IVUS transducer visualizes the aorta lumen, and the imaging information provides guidance for EIS characterization of the plaques by aligning the EIS sensor (2-point electrode) at the plaque. The IVUS transducer (center frequency between about 10 MHz and 60 MHz) is cannulated through the inner catheter to the imaging window where it rotates at 100-2400 revolution per minute (RPM) to scan the endolumen. The EIS sensor is affixed and mounted on a balloon, which is deflated during cannulation and is inflated for EIS measurement. PBS: Phosphate-buffered saline solution.
FIG. 2B is a conceptual illustration depicting the design of an exemplary integrated sensor highlighting the mechanism for IVUS-guided EIS measurement. The IVUS transducer is positioned inside the inner catheter (ID: 1 mm, OD: 1.3 mm) with an imaging window of 1 cm to 10 cm. The EIS sensor is affixed to the balloon, which is anchored to the outer catheter (ID: 1.7 mm, OD: 2 mm). External pump generates air pressure to inflate or deflate the balloon, ranging from 1 mm to 15 mm in diameter.

IVUS imaging visualizes the endoluminal surface, eccentricity of the plaque, intraplaque echogenicity and arterial wall thickness (Ma J et al., Applied physics letters 106.11 (2015): 111903). The mechanically scanning IVUS transducer (20~45 MHz) or the radial array transducer (10~20 MHz), transmitting and receiving the high frequency ultrasonic waves, is capable of delineating the cross-sectional anatomy of coronary artery wall in real time with 70 to 200 µm axial resolution, 200 to 400 µm lateral resolution, and 5 to 10 mm imaging depth (Brezinski M E et al., Heart 77.5 (1997): 397-403; Elliott M R et al., Physiological measurement 17.4 (1996): 259). For these advantages, simultaneous IVUS-guided EIS measurement enabled precise alignment of the visualized plaques with the balloon-inflatable EIS sensor; thereby, providing both topological and biochemical information of the plaque (FIG. 2A). Ex vivo assessment of NZW rabbit aortas was performed after 8 weeks of high-fat diet, and the results demonstrated significant reproducible measurements in both impedance and phase (p-value<0.05) via IVUS-guided EIS assessment. Thus, the integrated sensor design enhanced IVUS-visualized plaques and EIS-detected oxLDL to assess metabolically unstable plaques with clinical implications in reducing procedure time and X-rays exposure.

The methods and materials are now described.

Integrated Sensor Design

Built on prior intravascular techniques (Cao H et al., Biosensors and Bioelectronics 54 (2014): 610-616; Yu F et al., Biosensors and Bioelectronics 43 (2013): 237-244), the catheter-based dual sensors cannulate through aortas to reach the lesion sites for detection (FIG. 2A). While advancing, the balloon is deflated (inset of FIG. 2A) and the whole diameter of the exemplary sensor embodiment is 2.3 mm. When the sensor reaches the detecting sites, the IVUS transducer scans the section of aorta through the imaging window by rotating and pulling-back. In case lesion sites are detected, the whole sensor is further advanced and rotated to align the EIS sensor at the lesion sites. Air is then pumped though the outer catheter to inflate the balloon, allowing the 2-point electrodes to make contact with the lesions. EIS measurement is performed and the impedance characteristics indicate the presence or absence of intraplaque lipid (oxLDL).

Performance of the integrated sensor was established by the IVUS-visualized endolumenal plaque and EIS-detected intraplaque oxLDL (FIG. 2B). The two sensors were intravascularly deployed by two layers of catheters bonded together at the end of the outer layer. The 45 MHz IVUS transducer (Li X et al., IEEE transactions on ultrasonics, ferroelectrics, and frequency control 61.7 (2014): 1171-1178) was enclosed in the inner catheter at the imaging window while the EIS sensor was affixed to a balloon that was anchored on the outer catheter. The inner catheter was designed to be longer than the outer catheter by ~2-10 cm for the IVUS imaging window.

The IVUS imaging process required the acoustic wave to reach aorta walls and echo back to the IVUS transducer. For this reason, the inner catheter was acoustically transparent with matched impedance and low attenuation; thereby, allowing for acoustic wave penetration. The acoustic impedance match was established by two strategies: 1) water or phosphate-buffered saline (PBS) was injected into the inner catheter, and 2) the IVUS catheter was longer than the outer catheter by 2-10 cm (preset length) to avoid the balloon or the outer catheter from obstructing the acoustic path. The rotational and pullback scanning were made possible by positioning the IVUS transducer in the inner catheter (outer diameter=1.3 mm). The transducer was navigated by a torque wire. The flexibility of IVUS transducer torque wire allowed for deployment into the inner catheter.

The optimal EIS signal was demonstrated by inflating the balloon, allowing the 2-point electrode array to be in transient contact with the lumen. The balloon was mounted on the outer catheter (outer diameter=2 mm and inner diameter=1.7 mm). The IVUS first scanned across the clear imaging window to visualize the lumen and plaques. Next, the EIS sensor was advanced to align with the IVUS window. Air was pumped through the gap between the inner and outer catheters to inflate the balloon for EIS measurement. These sequential steps effectively minimized the interference between the EIS sensor the IVUS acoustic pathway.

Principles of EIS

Figures 9A, 9B, 9C, 9D:
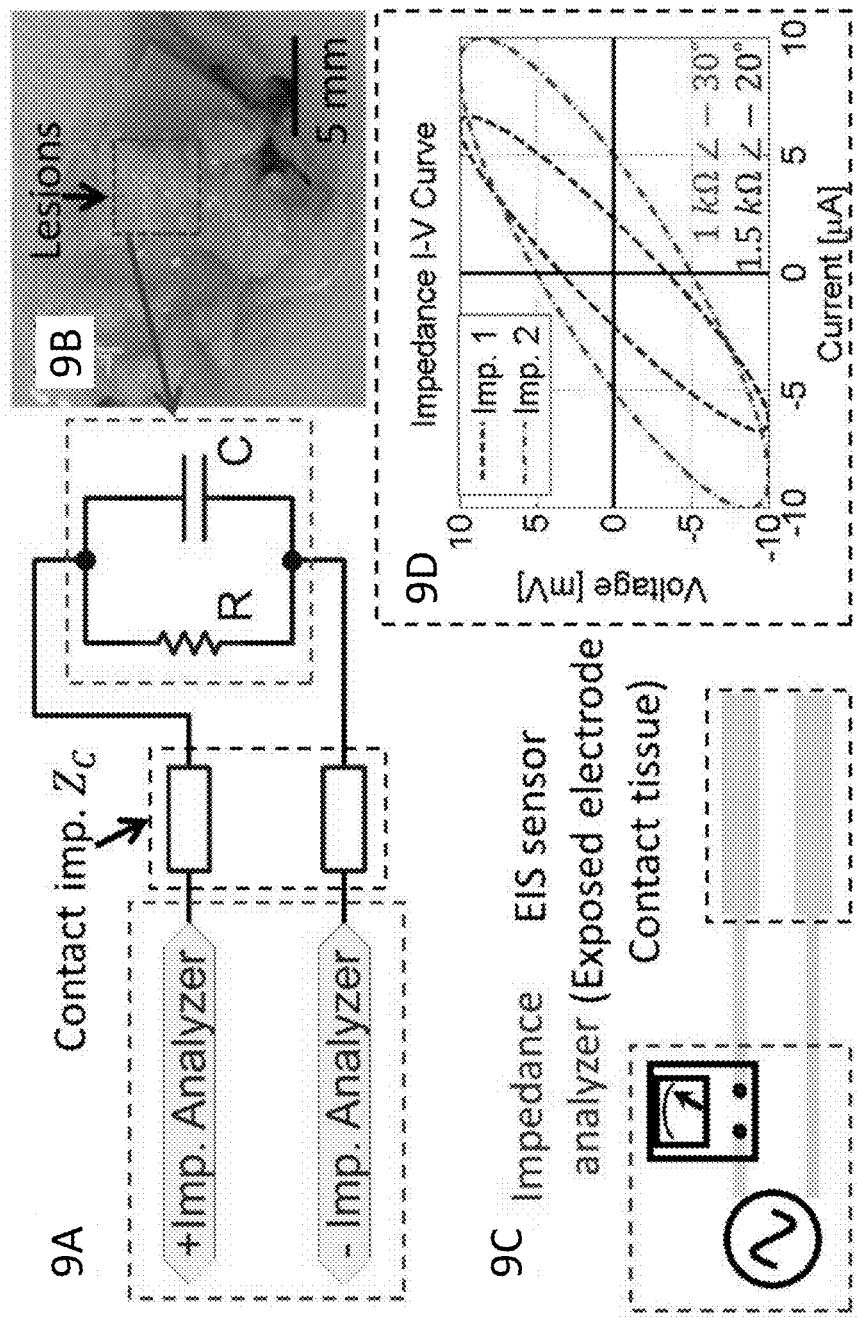
FIG. 9A depicts a schematic representation of an exemplary equivalent circuit for EIS measurement.
FIG. 9B depicts a lesion, wherein in an EIS system, the EIS sensor (exposed electrode) is attached to the specimen (e.g. aorta covered by plaques).
FIG. 9C depicts an illustration of the total impedance to include tissue and the contact interface.
FIG. 9D depicts a chart demonstrating that the impedance is recorded by an impedance analyzer, as illustrated by the current-voltage (I-V) curve to provide both magnitude and phase delay.

EIS is the macroscopic representation of the electric field and current density distribution within the specimen being tested (FIG. 9A through FIG. 9D). Applying quasi-electrostatic limits to Maxwell's equations, the field distribution can be described as follows (Larsson J et al., American Journal of Physics 75.3 (2007): 230-239):

$$\nabla \cdot (\sigma^* \nabla \varphi) = 0 \quad \text{(Eq. 1)}$$

where $\sigma^* = \sigma_T + j\omega\varepsilon_T$. $\sigma_T$ and $\varepsilon_T$ denote the conductivity and permittivity of the sample, respectively, $\omega$ the angular frequency, $j=\sqrt{-1}$, and $\varphi$ the voltage distribution. Current density, $\vec{J} = \sigma^* \vec{E}$, is calculated with the distribution of electric field, $\vec{E}$. Finally, electrical impedance of the sample, z, according to Maxwell's equations, is expressed as follows:

$$Z = \frac{\Delta \varphi}{\int_S \vec{J} \cdot d\vec{S}} \quad \text{(Eq. 2)}$$

where $\vec{S}$ denotes the electrode-tissue interface area, and $\Delta\varphi$ the voltage difference across the two electrodes of the EIS sensor. The resistance and reactance value of the impedance is represented as a resister, R, and a capacitor, C (FIG. 9A). Contact impedance, $Z_c$, at the interface between the electrode and tissue, is not negligible in most cases, and is taken into account in the measuring system as previously reported (Cao H et al., Biosensors and Bioelectronics 54 (2014): 610-616; Yu F et al., Biosensors and Bioelectronics 43 (2013): 237-244).

The electrochemical impedance signal consists of both magnitude and phase information (FIG. 9D). The low conductivity of oxLDL is the basis for an elevated magnitude in impedance in the oxLDL-laden plaques. In contrast, the high conductivity of healthy aorta walls exhibits lower impedance magnitude in response to the alternating current (AC). The complex impedance of the tissue is expressed as:

$$Z = \left(\frac{1}{j\omega C} // R\right) = \frac{R - j\omega CR^2}{1 + \omega^2 C^2 R^2} \quad \text{(Eq. 3)}$$

$$|Z| = \frac{R}{\sqrt{1 + \omega^2 C^2 R^2}} \quad \text{(Eq. 4)}$$

$$\phi = -\arctan(\omega CR) \quad \text{(Eq. 5)}$$

where $\omega$ is the angular frequency; and $\phi$ the phase.

Procedure

A two-point electrode was designed as the EIS sensor for this deep tissue penetration (Packard R R S et al., Annals of biomedical engineering 44.9 (2016): 2695-2706). The configuration of the two electrodes for the EIS sensor were identical at 3 mm in length and 0.3 mm in width, and were aligned in parallel at 0.3 mm kerf (gap) apart (inset of FIG. 2B, FIG. 9A). The 2-point electrodes made electrical contact with the plaques upon balloon inflation. During EIS assessment, AC current was driven through the plaque while maintaining a constant peak voltage. The current was recorded to calculate the electromagnetic impedance of the plaque in terms of impedance magnitude and phase (example in FIG. 9D). By swiping the frequencies, an impedance spectrum was acquired. The relatively long electrode (3 mm) and narrow kerf (0.3 mm) allowed for high current penetration through the plaques.

The flexible EIS sensor was fabricated on a polyimide substrate. Copper (12 μm) was deposited on the polyimide (12 μm) via plated-through-hole (PTH) methodology. Subsequently, the copper was selectively removed by chemical etching based on lithographically-defined pattern using dry film photoresist. A subsequent lamination was done to cover a majority of the copper area with a second layer of polyimide (12 μm), while leaving the sensor area exposed. Finally, Au/Ni (200 nm/20 nm) was immersion-coated on the exposed electrodes. The polyimide substrate is not stretchable, which ensures that the EIS sensor is free from cracking or discontinuities. The leading wires (30 cm long) were copper layers fabricated together with the sensor and covered by the second polyimide layer. The proximal end of the leading wires was connected to a Series G 300 Potentiostat (Gamry Instruments Inc., PA, USA) for EIS measurement.

EIS measurements were deployed to the ex vivo aortas from NZW rabbit in the presence or absence of IVUS guidance. Five control rabbits fed on a normal chow diet (n=5) and 3 age-matched high-fat fed NZW male rabbits (n=3) were analyzed (Anichkov 1955; Anichkov and Volkova 1954; Anitschkow et al. 1983). High-fat animals were placed on a 1.5% cholesterol and 6.0% peanut oil diet (Harlan Laboratory). After 9 weeks, thoracic aorta sections were dissected for the IVUS-guided EIS measurements. The ultrasound transducer rotated in the inner catheter to acquire the cross-sectional imaging around the catheter. The ultrasonic A-lines were acquired every 0.65 degrees and 550 A-lines were acquired in each frame. After digitization, the echo signal was filtered with pass band between 10 MHz and 100 MHz.

After localizing the plaques, the balloon catheter (FIG. 2A) was advanced to align with the lesion sites. The balloon was inflated at ~2 atm (~200 kPa), facilitating the EIS sensors in contact with the lumen or lesions for assessing the electrical impedance. Alternative voltage (50 mV amplitude) was applied to the 2-point electrodes, and the current was measured to determine the electrical impedance at the frequency swipes from 100 Hz to 300 kHz. A similar approach was performed without IVUS guidance. The individual measurements were repeated 5 times.

The IVUS-guided images and EIS measurements were validated by histology. The aortic segments were fixed in 4% paraformaldehyde, embedded in paraffin and serially sectioned at 5 μm for histological analyses. Lipids were identified by Hematoxylin and Eosin (H&E) staining and oxLDL-laden macrophages by F4/80 staining (monoclonal rat anti-mouse antibody, Invitrogen).

Statistical analysis analyzed the significance of EIS results. Average and standard deviation demonstrated the impedance characteristics and the measurement variability. A distinct differentiation between oxLDL-laden and lesion-free aortas indicated a preferable impedance characterization. Student's t-test and analysis of variance with multiple comparisons adjustment were performed. A p-value<0.05 was considered statistically significant.

The results are now described.

Integrated Sensor

Figures 10A, 10B, 10C:
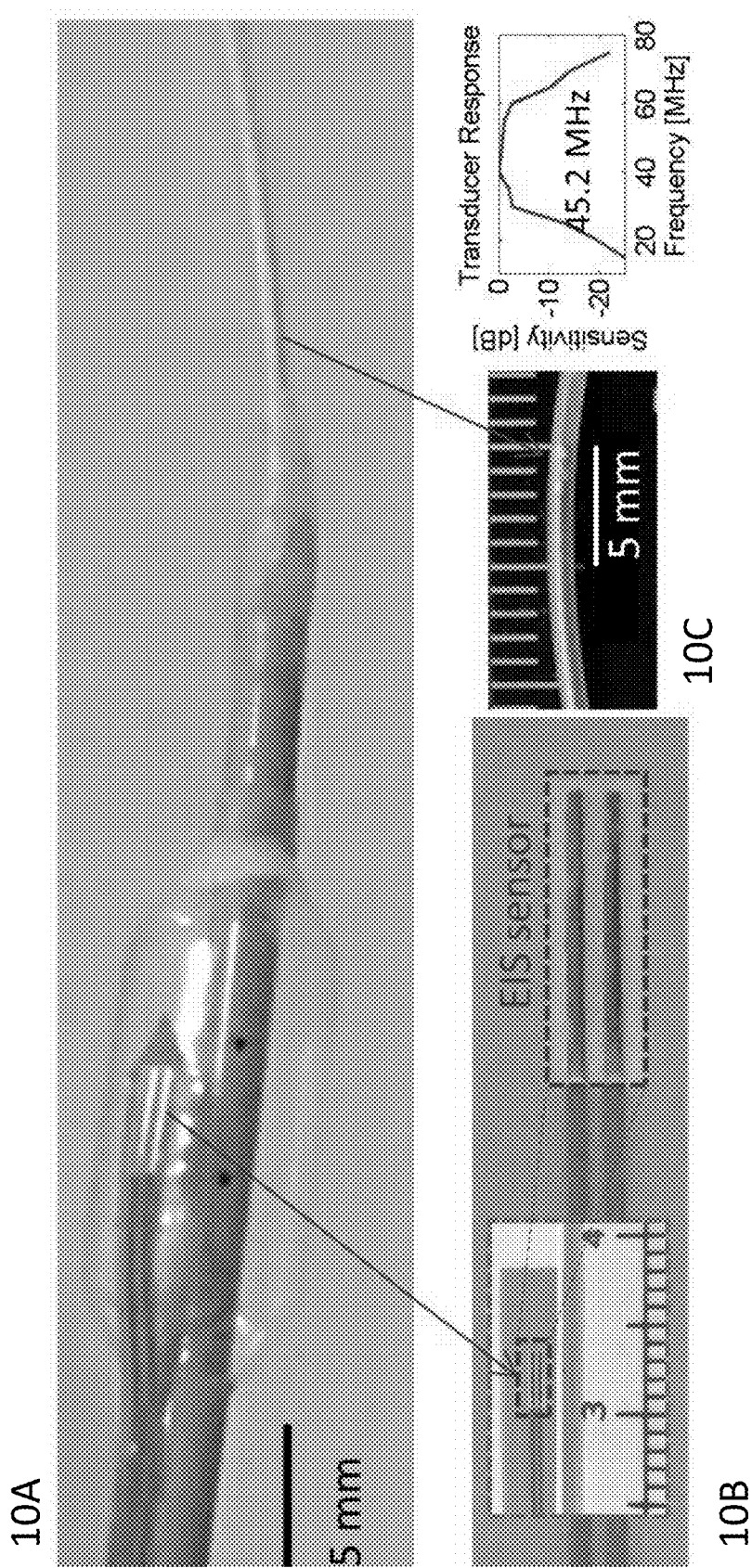
FIG. 10A through FIG. 10C depict an exemplary integrated sensor.

A prototype of the integrated sensor consisted of an EIS sensor and an IVUS transducer (FIG. 10A). The two sensors, 2-point electrodes and ultrasonic transducer, were fabricated individually, followed by integration for the catheter-based deployment to assess oxLDL-laden plaques. The two-point electrodes for EIS sensor (Packard R R S et al., Annals of biomedical engineering 44.9 (2016): 2695-2706) was fabricated on polyimide by depositing Au/Ni electrode, and the leading wires were embedded by a second layer of polyimide while an opening at the distal end allowing for the EIS sensing (FIG. 10B). The IVUS transducer (Li X et al., IEEE transactions on ultrasonics, ferroelectrics, and frequency control 61.7 (2014): 1171-1178) was mounted on a rotational shaft to generate radial cross-sectional images of the aortas. Interference between the two elements was minimized by separating them spatially. The IVUS transducer was positioned in the acoustic image window distal to the balloon and EIS sensor.

Intravascular ultrasound imaging visualized the topography of the aorta and identified the endoluminal atherosclerotic lesions. The plaques were identified by their distinct scattering characteristics (inset of FIG. 11A and FIG. 11B). In the IVUS-guided measurement, the EIS sensor was steered to the endoluminal sites to assess the eccentric plaques present in the thoracic aorta. In contrast, random EIS measurements were performed without the IVUS-guidance to compare variability and reproducibility.

Electrochemical Impedance Spectroscopy

Figures 11A, 11B, 11C, 11D, 11E, 11F:
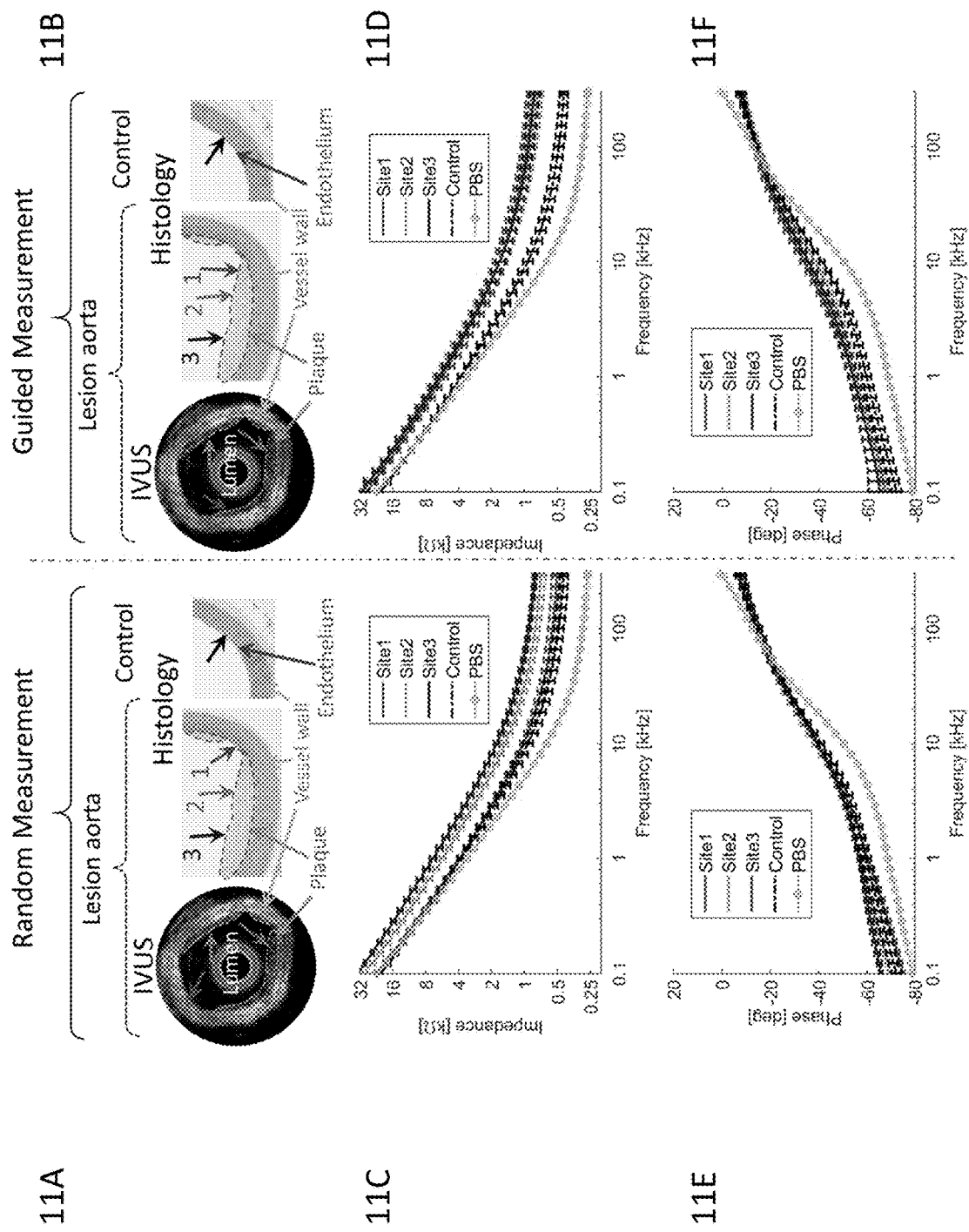
FIG. 11A through FIG. 11F depict the results of experiments demonstrating the performance of an exemplary integrated transducer by comparing random (non-guided) and guided measurements.

In both the IVUS guided- and non-guided EIS measurements, the mean values of the impedance magnitude (kΩ) in oxLDL-laden plaque were elevated as compared to the control (FIG. 11C, FIG. 11D). The non-IVUS-guided EIS harbored a wide range of standard deviations, with the lower limits overlapping with those of control (FIG. 11C), likely from misalignment with the plaque. In the case of random measurement, EIS at Sites 2 and 3 aligned with the lesion, resulting distinct impedance magnitude, whereas EIS measurement at Site 1 (lesion free) was indistinct from the control. In the case of IVUS-guided measurement, the EIS measurements were aligned with the lesions, resulting in reduced standard deviations and increased frequency-dependent separation from those of control across the entire frequency range (100 Hz-300 kHz) (FIG. 11F).

In addition to the impedance magnitude, the phase (ϕ) spectra provided an alternative detection for the oxLDL-laden lesions (FIG. 11E, FIG. 11F). As supported by Eq. (5) and corresponding analysis, the phase of all the measurements overlapped at high frequencies (>20 kHz). The optimal phase separation between lesion sites and control occurred at <15 kHz. In the random measurements, the phases of lesion sites overlapped with the control (FIG. 11E), while in the guided measurement the lesion sites were distinct at <15 kHz (FIG. 11F).

Figures 12A, 12B:
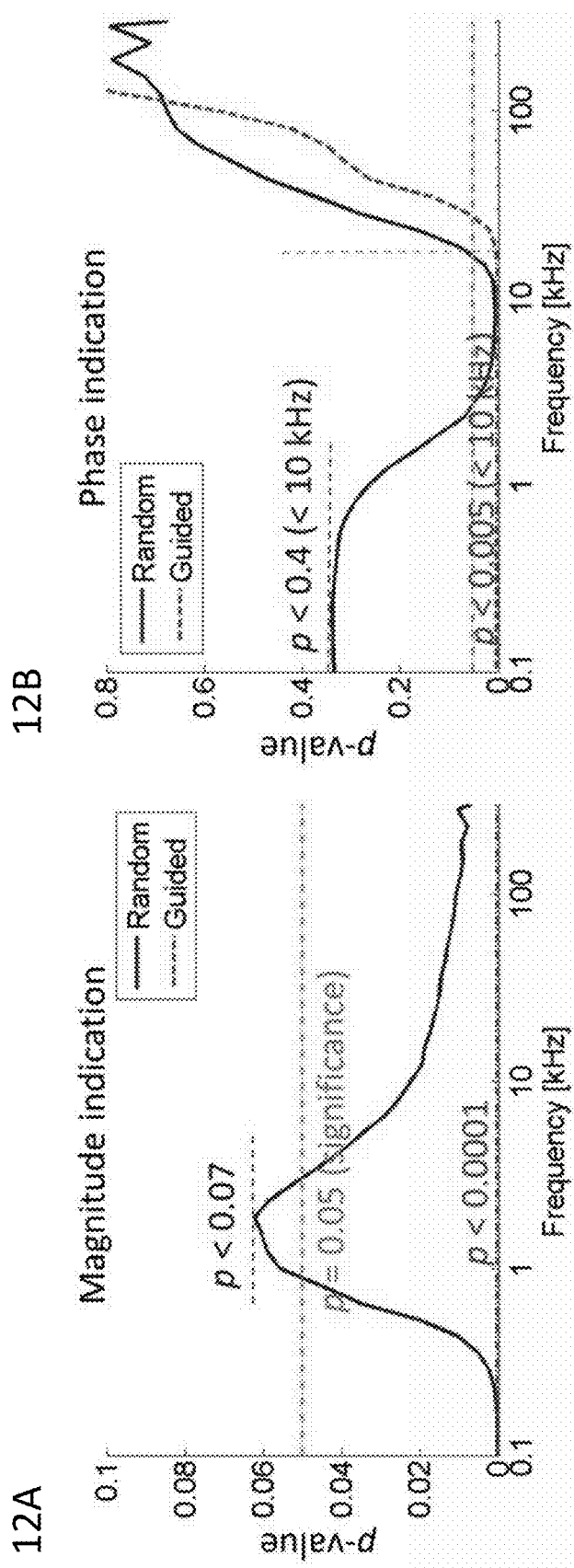
FIG. 12A depicts the results of statistical analysis of magnitude measurements. The random measurement showed insignificant p-value ($p<0.07$) while the guided measurement resulted in consistent results ($p<0.0001$).
FIG. 12B depicts the results of statistical analysis demonstrating significant differences between the random and guided measurements. The random measurements resulted in insignificant result ($p<0.4$) while the guided measurement resulted in significant result ($p<0.005$) at <15 kHz. At high frequencies, even guided measurements were statistically insignificant ($p>0.05$).

Statistical analysis demonstrated the EIS measurements with and without IVUS guidance (FIG. 11A through FIG. 11F). In the case of IVUS guidance, impedance magnitude (kΩ) at Sites 2 & 3 was distinct from control, whereas measurement at Site 1 was insignificant. EIS measurements were statistically insignificant considering all results (FIG. 12A). IVUS-guided EIS measurements demonstrated statistically significant differences with the added advantage of smaller data spread in a given condition leading to smaller standard deviations (p<0.0001) (FIG. 12A). Phase delay, an alternative measure derived from EIS, demonstrated similar trends (FIG. 12B). Significant statistics were observed at <20 kHz with IVUS-guidance, whereas insignificance exhibited throughout the frequency range without IVUS-guidance.

The novelty of the current work resides in the integrated sensor design to enable IVUS-guided EIS assessment of metabolically unstable plaque. The double-layer catheter allowed for the flexible 2-point electrodes to affix to the balloon anchored to the outer catheter while the rotating ultrasonic transducer was deployed to the inner catheter. The imaging window distal to the balloon provided matched acoustic impedance, enabling the high-frequency transducer (45 MHz) to visualize the vessel lumen and 2-point electrode to align with the plaques. Upon balloon inflation, oxLDL-laden plaques exhibited statistically distinct EIS measurements. Thus, the present study introduces the first IVUS-guided EIS sensor to detect intraplaque oxLDL with reduced standard deviation and increased statistical significance in both impedance and phase delay.

The integrated sensor strategy paves the way to diagnose vulnerable plaques to predict acute coronary events or stroke. The non-guided EIS measurements require repeated trials at multiple sites in need of deflating and re-inflating of the balloon, prolonging procedure time and fluoroscopy X-rays exposure, whereas the IVUS imaging prior to EIS measurement visualizes the anatomy to enable precise alignment with lesions for EIS measurement. Statistically significant results were obtained by the IVUS-guided EIS measurement (p<0.0001 for magnitude and p<0.005 for phase within 15 kHz), whereas measurements without the guidance reduced the significance (p<0.07 for magnitude and p<0.4 within 15 kHz). As a result, reliable detection of intraplaque oxLDL was obtained from a single measurement, reducing patient exposure to radiation and operation time.

The advent of near-infrared fluorescence (NIRF) provides cysteine protease activity as an indicator of inflammation (Weissleder R et al., Nature biotechnology 17.4 (1999): 375-378), and the use of glucose analogue [18F]-fluorodeoxyglucose (18FDG) reveals metabolic activity by Positron Emission Tomography (PET) (Rudd J H F et al., Circulation 105.23 (2002): 2708-2711). However, injection of contrast agents is required for NIRT and radioactive isotopes PET imaging. Using concentric bipolar microelectrodes for EIS measurements, significant frequency-dependent increases were previously demonstrated in EIS magnitude among fatty streaks (Stary Type II lesions), fibrous cap oxLDL-rich (Type III or IV), oxLDL-free (Type V), and calcified lesions (type VII) (Yu F et al., Biosensors and Bioelectronics 30.1 (2011): 165-173). To enhance the specificity, the present study hereby established a dual sensing modalities, integrating ultrasound (IVUS) and electrochemical impedance (EIS) for early detection of the mechanically and metabolically unstable lesions (FIG. 13). The integrated sensing modalities allow initial identification and visualization by IVUS, then electrochemical characterization by EIS.

In addition to the electrochemical (EIS) strategy, alternative techniques have been developed to assess the thin-cap fibroatheroma (Kolodgie F D et al., Current opinion in cardiology 16.5 (2001): 285-292; Virmani R et al., Progress in cardiovascular diseases 44.5 (2002): 349-356; Virmani R et al., Journal of the American College of Cardiology 47.8 Supplement (2006): C13-C18) and intraplaque angiogenesis (Doyle B et al., Journal of the American College of Cardiology 49.21 (2007): 2073-2080; Khurana R et al., Circulation 112.12 (2005): 1813-1824; Purl R et al., Nature Reviews Cardiology 8.3 (2011): 131-139) for plaque vulnerability. Integrated IVUS and optical coherence tomography (OCT) catheters were developed to acquire high resolution thin fibrous cap and the underlying necrotic core simultaneously (Li X et al., IEEE Journal of Selected Topics in Quantum Electronics 20.2 (2014): 196-203). Whereas the incremental imaging data helps determine the characteristics of plaque, the OCT technique is limited by the need to avoid the light scattering by the red blood cells. For this reason, saline solution flushing is essential for imaging acquisition (Li X et al., IEEE Journal of Selected Topics in Quantum Electronics 20.2 (2014): 196-203). In the setting of acute coronary events, transient lack of blood perfusion is clinically prohibitive. Photoacoustics is an emerging approach based on the high photo-absorption and thermal expansion of blood, and has been applied to image angiogenesis (Wang L V et al., Nature photonics 3.9 (2009): 503-509; Wang L V et al., Science 335.6075 (2012): 1458-1462; Xu M et al., Review of scientific instruments 77.4 (2006): 041101). Intravascular photoacoustics enables to image vasa vasorum and intraplaque micro-vessels visualization (Jansen K et al., Optics letters 36.5 (2011): 597-599; Wang B et al., Optics express 18.5 (2010): 4889-4897; Wang B et al., IEEE Journal of selected topics in Quantum Electronics 16.3 (2010): 588-599). However, the heat generated from thermal expansion poses an adverse effect on the vulnerable plaque (Stefanadis C et al., Circulation 99.15 (1999): 1965-1971). For intravascular photoacoustic imaging, the blood in the arteries absorbs light energy to the same or greater extent than that of vasa vasorum, resulting in obstruction to the intravascular photoacoustic imaging. Similar to OCT, saline flushing to remove red blood cells is essential (Wang B et al., IEEE Journal of selected topics in Quantum Electronics 16.3 (2010): 588-599). Acoustic angiography (Gessner R et al., IEEE transactions on ultrasonics, ferroelectrics, and frequency control 57.8 (2010): 1772-1781; Gessner R C et al., Journal of Biomedical Imaging 2013 (2013): 14) took advantage of high nonlinearity of microbubble contrast agents (Lindner J R et al., Nature Reviews Drug Discovery 3.6 (2004): 527-533; Lindner J R et al., Journal of the American Society of Echocardiography 15.5 (2002): 396-403) that were carried to micro-vessels by circulation, exciting them at fundamental frequency and detecting at high frequency super harmonics. Dual frequency intravascular ultrasound transducers (Ma J et al., IEEE transactions on ultrasonics, ferroelectrics, and frequency control 61.5 (2014): 870-880; Ma J et al., Physics in medicine and biology 60.9 (2015): 3441) were designed (Ma J et al., Applied physics letters 106.11 (2015): 111903) to visualize the vasa vasorum and intraplaque vasculature. The acoustic angiography techniques benefited from larger penetration depth and free of heating. The primary limitation of dual frequency harmonic imaging is its dependence on microbubble injection. Presence of microbubbles also engenders high scattering for the harmonic signals in the vasa vasorum. Occlusion of blood flow followed by saline flushing is also indicated. Besides super-harmonic imaging, the dual frequency IVUS enabled to image the thin-cap fibroatheroma with the high-frequency transducer (30 MHz) and the intraplaque oxidized lipid (oxLDL) with the low-frequency transducer (6.5 MHz) (Ma J et al., IEEE transactions on ultrasonics, ferroelectrics, and frequency control 61.5 (2014): 870-880). Unlike the aforementioned techniques, the IVUS-guided EIS assesses the biochemical property of plaques without the need to perform occlusion flushing. Furthermore, the aforementioned techniques focus on topological information (fibrous cap or vasculature), while the IVUS-guided EIS combines both anatomy and metabolic properties (oxLDL).

Example 3: 3-D Electrochemical Impedance Spectroscopy Mapping of Arteries to Detect Metabolically Active but Angiographically Invisible Atherosclerotic Lesions Electrochemical Impedance Spectroscopy (EIS) is the macroscopic representation of the electric field and current density distribution within the specimen being tested. EIS characterizes the dielectric properties of blood vessels and lipid-rich plaques (Yu F, et al., Biosensors and Bioelectronics 30, 165-173 (2011); Yu F, et al., Annals of Biomedical Engineering 39, 287-296 (2011); Yu F, et al., Biosensors and Bioelectronics 43, 237-244 (2013)). Applying quasi-electrostatic limits to Maxwell's equations, the field distribution is described as follows (Larsson J, American Journal of Physics 75, 230-239 (2007)):

$$\nabla \cdot (\sigma^* \nabla \varphi) = 0 \qquad (\text{Eq. 6})$$

where $\sigma^* = \sigma_T + j\omega\varepsilon_T$, $\sigma_T$ and $\varepsilon_T$ denote the conductivity and permittivity of the sample, respectively, $\omega$ the angular frequency, $j = \sqrt{-1}$, and $\varphi$ the voltage distribution. Current density, $\vec{J} = \sigma^* \vec{E}$, is calculated with the distribution of electric field, $\vec{E}$. Thus, electrical impedance of the sample, z, according to Maxwell's equations, is expressed as follows:

$$Z = \frac{\Delta\varphi}{\int_S \vec{J} \cdot d\vec{S}} \qquad (\text{Eq. 7})$$

where $\vec{S}$ denotes the electrode-tissue interface area, and $\Delta\varphi$ the voltage difference across the two electrodes of the EIS sensor. Intravascular ultrasound (IVUS)-guided EIS sensors detect atherosclerotic lesions associated with oxidative stress in fat-fed New Zealand White (NZW) rabbits (Ma J, et al., Sensors and Actuators B: Chemical 235, 154-161 (2016)). Specifically, vessel walls harboring oxidized low density lipoprotein cholesterol (oxLDL) exhibit distinct EIS values (Yu F, et al., Annals of Biomedical Engineering 39, 287-296 (2011)). However, atherosclerotic lesions are often eccentric and multiple. To detect these lesions, a novel 6-point electrode configuration for comprehensive 3-D endoluminal interrogation of angiographically invisible atherosclerosis was developed.

OxLDL (Sevanian A, et al., Arteriosclerosis, Thrombosis, and Vascular Biology 16, 784-793 (1996)) in atherosclerotic lesions display distinct frequency-dependent electrical and dielectrical properties (Suselbeck T, et al., Basic Res Cardiol 100, 446-452 (2005); Streitner I, et al., Atherosclerosis 206, 464-468 (2009)). Concentric bipolar electrodes were developed to assess elevated EIS signals in oxLDL-rich lesions from human coronary, carotid, and femoral arteries (Yu F, et al., Biosensors and Bioelectronics 30, 165-173 (2011)). By deploying the flexible and stretchable bipolar electrodes to the aorta of NZW rabbits, a significant increase in impedance magnitude was demonstrated in oxLDL-rich plaques (Yu F, et al., Annals of Biomedical Engineering 39, 287-296 (2011)). A 2-point micro-electrode configuration was further established to allow for deep intraplaque penetration via alternating current (AC) (Packard R R S, et al., Annals of Biomedical Engineering 44, 2695-2706 (2016)). The frequency sweep from 10 to 300 kHz generated an increase in capacitance, providing distinct changes in impedance (Ω) in relation to varying degrees of aortic intraplaque lipid burden (Packard R R S, et al., Annals of Biomedical Engineering 44, 2695-2706 (2016)).

To advance intravascular EIS interrogation for 3-D endoluminal plaque detection, the following study investigates a 6-point electrode configuration to enable 15 alternating electrochemical impedance spectroscopy (EIS) permutations of 2-point electrode arrays for comprehensive impedance mapping and detection of lipid-rich atherosclerotic lesions. The individual electrode configuration are identical in each row, where three electrodes are circumferentially and equidistantly positioned. In addition to optimal contact with the endoluminal surface, this new 6-point configuration enables 15 different pairs of electrodes to provide 3-D interrogation of the endoluminal area. The capability of 3-D EIS sensors to detect angiographically invisible early atherosclerotic lesions in different aortic segments from NZW rabbits on high-fat diet-induced hypercholesterolemia is demonstrated. The 3-D EIS measurements are in close agreement with the equivalent circuit model for aortas consisting of vessel tissue, atherosclerotic lesion, blood, and perivascular fat. Statistical analysis corroborates the 3-D EIS permutations for early atherosclerosis detection, with clinical implications to prevent acute coronary syndromes or strokes.

The materials and methods are now described.
Sensor Design and Fabrication

The newly designed 6-point EIS sensor featured six individual electrodes that were circumferentially mounted on an inflatable balloon (FIG. 5A). The individual electrodes were identical in dimensions (600 μm×300 μm) and connected to an impedance analyzer (Gamry Series G 300 potentiostat, PA) that was installed in a desktop computer. Specifically, there were three electrodes embedded in each row, and the distance between the two rows was 2.4 mm (FIG. 5B). Within each layer, the 3 electrodes were equidistantly placed around the circumference of the balloon at 120° separation from each other (FIG. 5C). This 6-point configuration optimized the contact with the endoluminal surface for EIS measurements. Furthermore, the 6 electrodes allowed for 15 different combinations of 2-point electrodes for 3-dimensional endoluminal interrogation.

Figures 6A, 6B, 6C, 6D, 6E:
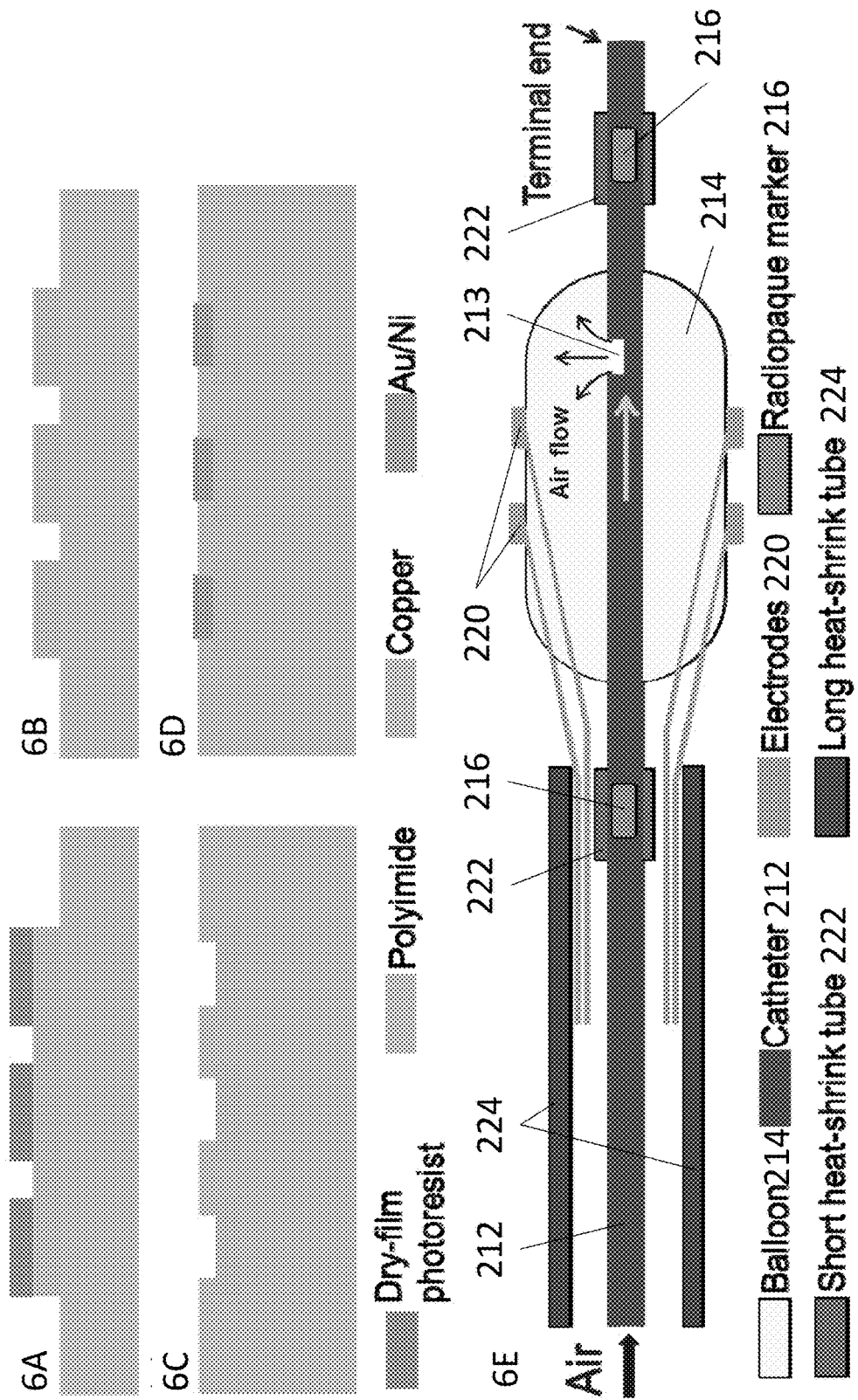
FIG. 6A through FIG. 6E illustrate the fabrication process of flexible electrodes.

To micro-fabricate the EIS sensors, flexible polyimide electrodes were first acquired (FPCexpress.com, Ontario, CA) with a nominal length of up to 1 meter to bypass the need for interconnects that are required between electrode pads and wirings (Packard R R S, et al., Annals of Biomedical Engineering 44, 2695-2706 (2016)). These flexible electrodes have been pre-constructed according to the pattern shown in FIG. 5A through FIG. 5D using the following process: a copper layer (12 μm) was deposited onto the polyimide substrate (12 μm) through electroplating, followed by selective chemical etching of the lithographically-defined patterns via the dry film photoresist (FIG. 6A, FIG. 6B). A second layer of polyimide (12 μm) was added to cover the majority of the copper area using a lamination process. The copper area that eventually became the electrode/contact pad was left uncovered. Finally, a layer of Au/Ni (50 nm/2000 nm) was added through electroless-nickel-immersion-gold (ENIG) process.

To develop the catheter-based device for intravascular deployment, the inflatable balloon (9 mm in length, 1 mm diameter under deflation and ~3 mm diameter under inflation, Ventiona Medical, NH) was mounted on the terminal end of the catheter (40 cm in length) (Vention Medical, NH). Miniature holes were designed to enable balloon inflation. A pair of tantalum foils (1×1 mm, Advanced Research Materials, Oxford, UK) was incorporated to both ends of the balloon as a radiopaque marker, and was secured by a short segment of heat-shrink tube (in green) (Vention Medical, NH). The front end of the flexible electrodes was mounted onto the balloon by the silicone adhesive (Henkel, CT), and the rest of the electrodes and the catheter were encapsulated with the insulating heat-shrink tube 40 cm long, amber (Vention Medical, NH). Electrical connection to the impedance analyzer (Gamry Series G 300 potentiostat) was made via the soldering wires on the exposed contact pads to the terminal end of the flexible electrodes. The prototype of the 6-point sensor comprised the radio-opaque markers, the inflatable balloon, and the electrodes packaged around the catheter (FIG. 5A through FIG. 5D). A mechanical pump (Atrion Medical Products Inc., Arab, AL) was connected to the end of the catheter to induce balloon inflation.

Equivalent Electrical Circuits

Figures 14A, 14B, 14C, 14D, 14E, 14F:
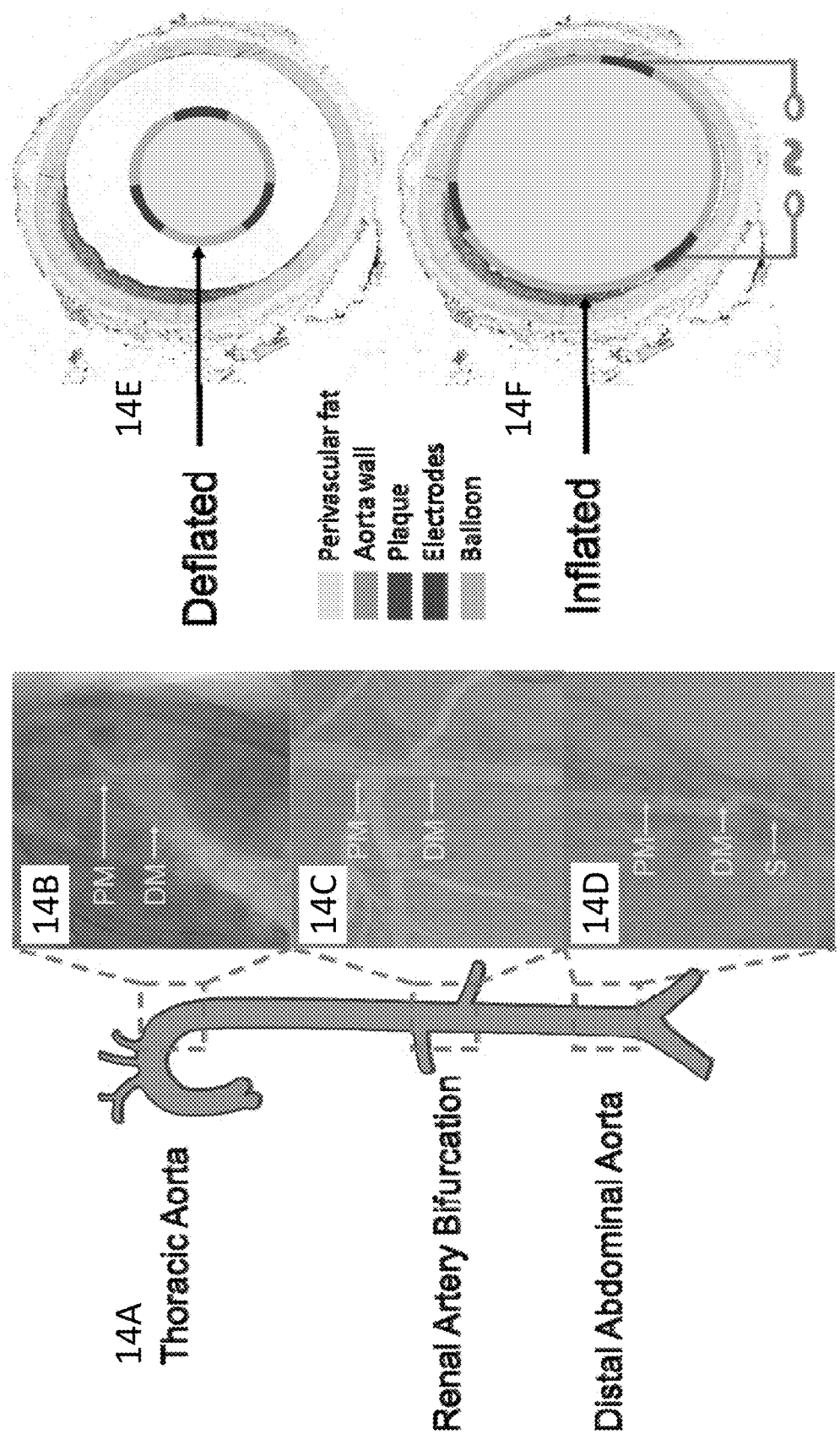
FIG. 14A through FIG. 14H illustrate in vivo sensor deployment and equivalent circuit modeling. The EIS sensor, identified on angiography by the proximal and distal markers, was deployed at 3 levels of the aorta (FIG. 14A): namely the thoracic aorta (FIG. 14B), the abdominal aorta at the level of renal artery bifurcation (FIG. 14C), and the distal abdominal aorta (FIG. 14D). The radiopaque markers made of tantalum (highlighted on the still angiograms by the black circle pointed to by the yellow arrows) permit the identification of the exact position of the device within the aorta. A cross-sectional perspective of the deflated (FIG. 14E) and inflated (FIG. 14F) balloon in the aorta shows specific electrodes to perform the endoluminal EIS measurement. The equivalent circuit includes the blood as primary circuit component upon balloon-deflation (FIG. 14G). The equivalent circuit further includes the aorta, plaque, blood, and pericardial fat all as the circuit components upon balloon-inflation (FIG. 14H). Legend. C: capacitive element. CPE: constant phase element. DM: distal sensor marker. Y: nominal capacitance value, $0<a<1$. PM: proximal sensor marker. R: resistive element. S: sheath.

Equivalent circuit models were developed to analyze the electrochemical impedance of atherosclerotic lesions at 3 distinct segments of the aorta (FIG. 14A through FIG. 14D) in the setting of balloon inflation and deflation (FIG. 14E, FIG. 14F). A cross-sectional perspective of the circuit configuration provides the operational principle underlying electrode-tissue interface for the endoluminal EIS interrogation. Four main types of tissue contribute to the aggregated impedance values; namely, blood, aortic wall, atherosclerotic plaque and perivascular fat circumscribing the vessel. In this context, a simple circuit block was first applied to generalize the impedimetric behavior of the individual tissues, consisting of a parallel circuit with two paths: 1) a resistive element ($R_1$) in series with a capacitive element (C) to model the cells; 2) a pure resistive element ($R_2$) to model the extracellular materials (red frame in FIG. 14G) (Aroom K R, et al., Journal of Surgical Research 153, 23-30 (2009)). The electrode-tissue interface was modeled using the constant phase element (CPE) to take into account the non-linear double layer capacitance behavior. The impedance of the interface can be expressed as:

$$Z_{CPE} = \frac{1}{Y(j\omega)^a} \quad \text{(Eq. 8)}$$

where Y denotes the nominal capacitance value, and a a constant between 0 and 1, representing the non-ideal interface effects.

Figures 14G, 14H:
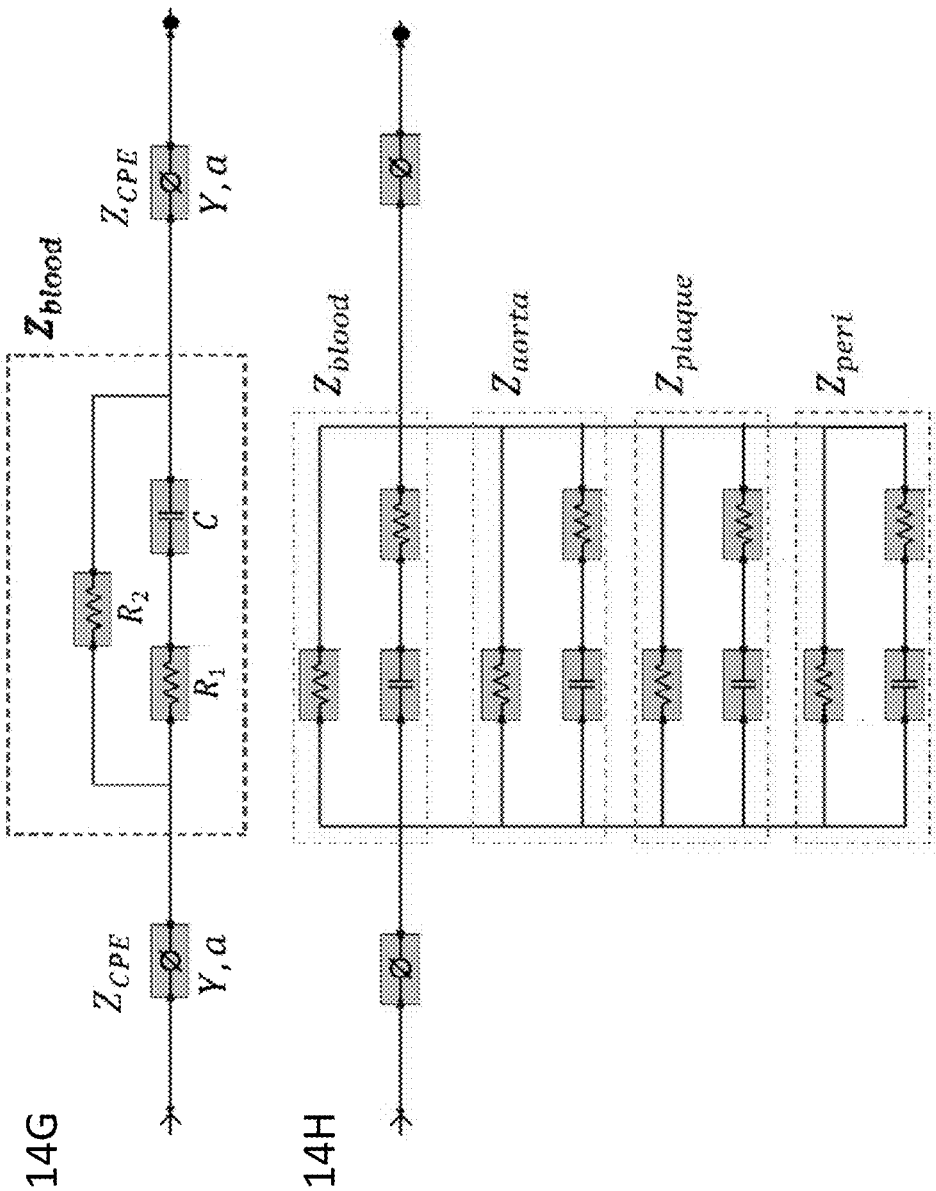

When the balloon was deflated, blood was included as the primary component ($Z_{blood}$) in the circuit model as other tissues were shielded by the presence of blood in contact with the electrodes (FIG. 14G). When the balloon was inflated, the endoluminal surface was in contact with the electrodes. As a result, all of the tissue types contributed to the path of the current flow, accounting for the parallel circuit configuration for the blood, plaque, vessel wall (aorta), and perivascular fat ($Z_{blood}//Z_{plaque}//Z_{aorta}//Z_{peri}$) (FIG. 14H).

Animal Model

Analyses were conducted in n=4 control rabbits fed a chow diet and n=5 age-matched high-fat fed NZW male rabbits (Cao H, et al., Biosensors and Bioelectronics 54, 610-616 (2014)). High-fat animals were placed on a 1.5% cholesterol and 6.0% peanut oil diet (Harlan laboratory) for 8 weeks prior to harvesting. Animals were anesthetized with isofluorane gas, endotracheally intubated and placed on a mechanical ventilator. A femoral cut-down was performed and a 4-French arterial sheath placed in the common femoral artery. Under fluoroscopic guidance (Siemens Artis Zeego with robotic arm) and iodinated contrast dye injection, the EIS sensor was advanced for in vivo interrogation of the distal abdominal aorta (site no. 1), followed by the aorta at the level of renal artery bifurcation (site no. 2), and finally at the level of the thoracic aorta (site no. 3). (FIG. 14A through FIG. 14D). Following animal harvesting, aortic samples from the 3 sites were sent for histological analyses. In the adopted scheme of high-fat feeding, these 3 anatomic sites corresponded to areas with trace atherosclerosis, or fatty streaks (abdominal aorta), and mild plaque (thoracic aorta) by histology.

EIS Measurement

EIS measurement was conducted along the aorta, namely, abdominal aorta proximal to the aortic bifurcation, abdominal aorta at the level of the renal artery bifurcation, and thoracic aorta. The device with radiopaque markers was placed at these pre-selected segments of the aorta via invasive angiography that was performed during fluoroscopy to mark the exact position of the endoluminal EIS measurements. During balloon inflation, a constant pressure at ~10 psi (pounds per square inch) was applied through a mechanical pump to establish contact with the endoluminal surface. EIS measurements were conducted using the Gamry system (Gamry Series G 300 potentiostat, PA, USA). At each interrogation site, two replicates of each fifteen permutations were performed. AC signals with peak-to-peak voltages of 50 mV and frequencies ranging from 1-300 kHz were delivered at each site. The impedance magnitudes were acquired at 10 data points per frequency decade.

Histology

After euthanasia, rabbits were perfused through the left ventricle with normosaline followed by 4% paraformaldehyde. Following fixation, aortic segments which had been identified in vivo by the radiopaque markers and interrogated during invasive angiography, were marked based on anatomic landmarks, excised, and samples sent to the CVPath Institute (Gaithersburg, MD) for further processing and staining. Following cryosectioning, samples were stained with hematoxylin and eosin and oil-Red-O for neutral lipids. Atherosclerotic areas identified by oil-Red-O were quantified using image J software (National Institutes of Health, Bethesda, MD).

Statistical Analyses

To test for differences in impedance values, the Brown-Forsythe test was used to determine significance across groups, and Dunnett's test was used for multiple comparisons and correction of multiple testing. Impedance values were further compared using the Mann-Whitney test for differences in medians, and the Kolmogorov-Smirnov test for differences in global value distributions. GraphPad version 6 was used to perform the statistical analyses. A P-value<0.05 was considered significant.

The results are now described

Intravascular Deployment for EIS Permutations

Impedimetric interrogation was demonstrated in the thoracic aorta, abdominal aorta at the level of the renal artery bifurcation, and abdominal aorta proximal to the aortic bifurcation (FIG. 14A through FIG. 14D). Prior to the EIS measurements, angiographic images were obtained to localize the EIS sensors as demarcated by the radiopaque tantalum pairs. Invasive angiography was unable to detect early atherosclerotic lesions (FIG. 14B through FIG. 14D). Invasive angiography was unable to detect early atherosclerotic lesions (Kashyap V S et al., Journal of Endovascular Therapy 15.1 (2008): 117-125) in high-fat diet fed rabbits (FIG. 14B through FIG. 14D). A representative schematic of the intravascular sensor with deflated (FIG. 14E) and inflated (FIG. 14F) balloon is shown. The equivalent circuit includes the blood as primary circuit component upon balloon-deflation (FIG. 14G, FIG. 21A). The equivalent circuit further includes the aorta, plaque, blood, and pericardial fat all as the circuit components upon balloon-inflation (FIG. 14H, FIG. 21B).

3-D EIS Mapping

Figures 15A, 15B, 15C, 15D, 15E, 15F, 15G:
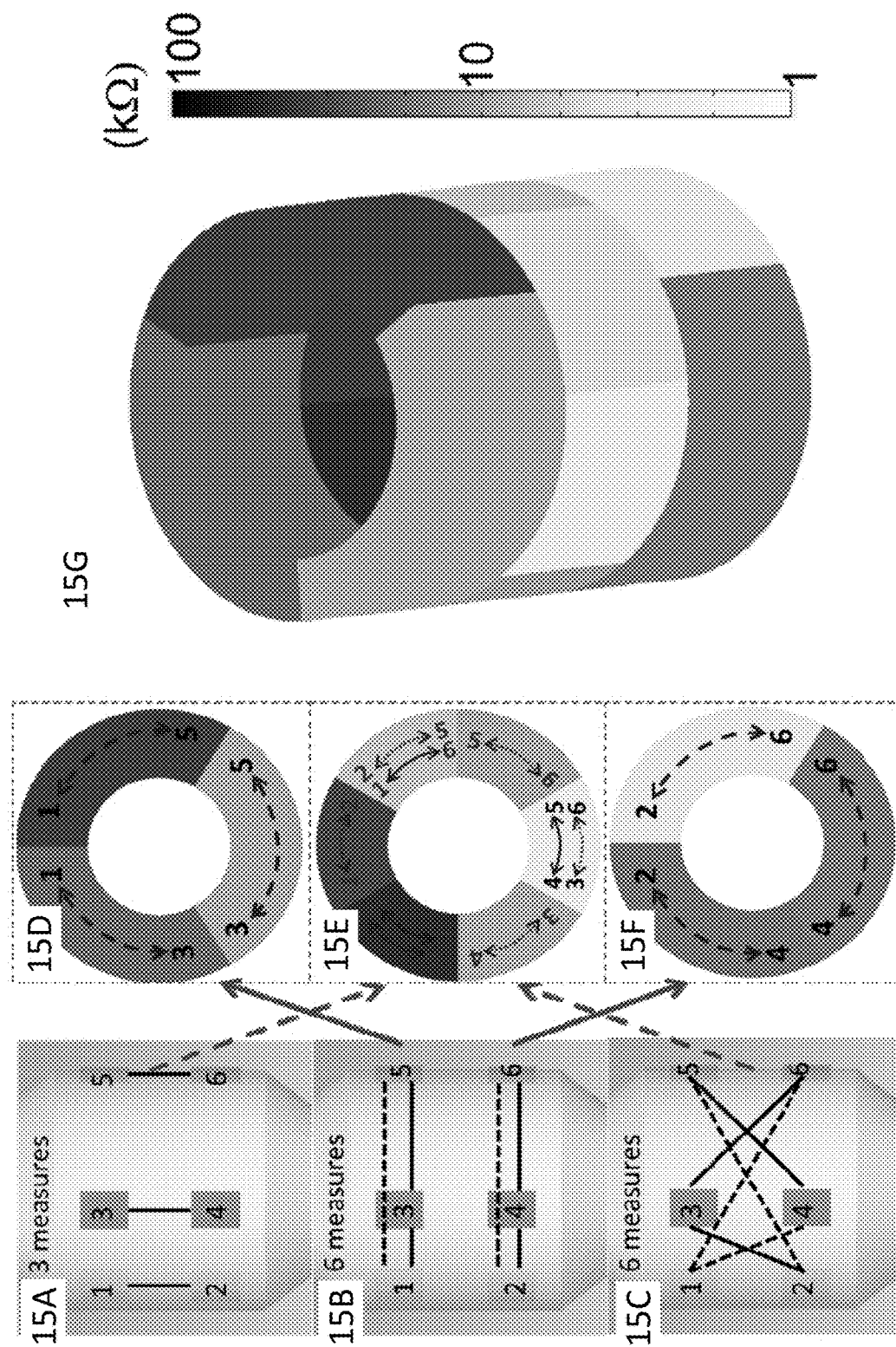
FIG. 15A through FIG. 15G depict 3-D EIS mapping using the 15 permutations of the 6-point device. There are 6 electrodes in the device and the individual pairs of electrodes are connected by the solid/dotted lines, each representing one permutation. The design of the 6-point EIS sensor into 2 rows, or rings, of 3-point electrodes permits 3 sets of long axis (vertical) interrogations (FIG. 15A), 6 sets of short axis (horizontal) interrogations (FIG. 15B), and 6 sets of diagonal interrogations (FIG. 15C).

The 6-point electrode configuration enabled the demonstration of 15 EIS permutations (3+6+6) consisting of three 2-point electrodes that were vertically linked between the two rows (FIG. 15A), six 2-point electrodes that were linked circumferentially within rows (FIG. 15B), and six 2-point electrodes that were cross-linked diagonally between the two rows (FIG. 15C). This novel combination of 15 permutations paved the way for flexible 3-dimensional interrogation and impedimetric mapping of the arterial segment over 3 rings, or sub-segments, as illustrated (FIG. 15D through FIG. 15F). For the 3-D mapping, each color represents impedance values using a distinct electrode permutation (FIG. 15G), with lighter colors indicating lower impedances and darker colors higher impedances, as illustrated using a logarithmic scale. This user-friendly readout permits rapid clinical impedance interpretation of lesion types, detection of clinically silent atherosclerosis, and physician adoption based on usability.

EIS Measurements

Figures 16A, 16B, 16C, 16D, 16E, 16F, 16G, 16H, 16I, 16J, 16K, 16L:
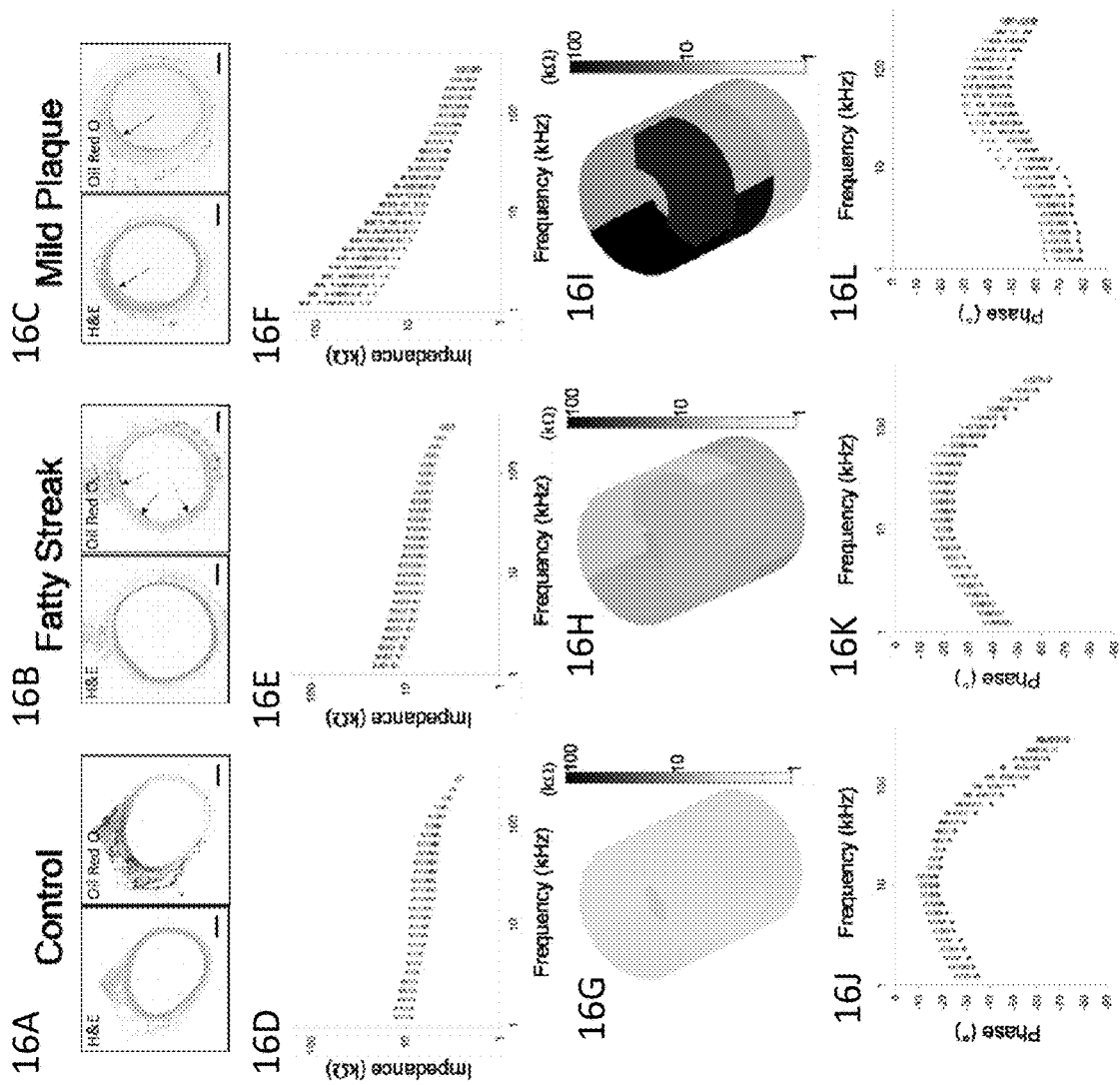
FIG. 16A through FIG. 16L depict EIS measurements and corresponding histology. Hematoxylin & eosin (H&E) staining was used for arterial wall and oil-Red-O for the lipid-laden atherosclerotic lesions to validate the EIS impedance measurements in control aortas (FIG. 16A, FIG. 16D), in fatty streaks from abdominal aortas (FIG. 16B, FIG. 16E), and in mild atherosclerotic plaques from the thoracic aorta (FIG. 16C, FIG. 16F). Eccentric plaques developed in the New Zealand White rabbits on high-fat diet in the thoracic aorta area (FIG. 16C, solid arrows), whereas much smaller, early atherosclerotic lesions, or fatty streaks, developed in the two abdominal sites (FIG. 16B, dotted arrows). Corresponding examples of the EIS impedance magnitude obtained from the 15 interrogations in response to the sweeping frequency from 1-300 kHz are presented in logarithmic scale (FIG. 16D, FIG. 16E, FIG. 16F). The reconstruction of the 15 permutation measures are represented in 3-D color coded impedance maps, visually demonstrating differences between control (FIG. 16G), fatty streak (FIG. 16H), and mild atherosclerotic plaque (FIG. 16I). Corresponding phase plots are also presented in logarithmic scale (FIG. 16J, FIG. 16K, FIG. 16L). Scale bar: 1 mm.

Representative real-time EIS measurements of impedance and phase are compared among the three segments of the aorta and correlated with histological findings (FIG. 16A through FIG. 16L). Histology staining with oil-Red-O for atherosclerotic lesions supported the changes in EIS in response to the eccentric plaques from the thoracic aorta to the renal bifurcation and distal abdominal aorta (FIG. 16A through FIG. 16C). Early lesions, also known as fatty streaks, stained positive for intra-lesion neutral lipids by oil-Red-O (FIG. 16E). The sweeping frequency ranged from 1-300 kHz within which the impedance decreased monotonously across conditions. Differences in impedance were most significant at 1 kHz (FIG. 16D through FIG. 16F). In the 3-D impedance map, lighter colors (yellow) were observed in control aortas (FIG. 16C), intermediate colors (yellow, light brown) in fatty streaks (FIG. 16G), and darker colors (dark brown, black) were present in the atherosclerotic plaques (FIG. 16K). Furthermore, increasing delays in phase were identified with lesion progression from control (FIG. 16J) to fatty streak (FIG. 16K) to mild plaque (FIG. 16L). The behavior of the EIS measurements was reflective of the heterogeneous composition of the atherosclerotic lesions.

Equivalent Circuit Modeling

Equivalent circuits were modeled to predict changes in EIS in response to balloon deflation and inflation (FIG. 14A through FIG. 14H). The model parameters (FIG. 14G, FIG. 14H) were numerically calculated by using a simplex algorithm available in the Gamry Echem Analyst software. Curve fitting was performed by incorporating the model parameters, namely; blood, vessel tissue, plaque, and perivascular fat. The theoretical curve fittings were in agreement with the experimental EIS measurements of impedance ($\Omega$) (FIG. 17A) and phase (°) (FIG. 17B) in response to balloon deflation and inflation. Under the deflation state, the electrodes were in contact with the highly conductive blood, and the model parameters for the vessel tissue, lipid-rich plaques, and perivascular fat were electrically shielded for the equivalent circuit model (FIG. 14E, FIG. 14G, FIG. 17A, FIG. 17B). Under the inflation state, the electrodes were in contact with the endoluminal surface and/or plaque, plus the additional model parameters from the vessel wall (FIG. 14F, FIG. 14H, FIG. 17A, FIG. 17B). The constant phase element can be described by the two variables Y and a. Our fitting results in both balloon deflated and inflated condition for Y/a are 321 nS·sa/0.691 (where n=nano, S=Siemens, and s=seconds) and 248 nS·sa/0.659, respectively, which indicates there is no significant distinction between the two scenarios in terms of contact impedance.

Figure 18:
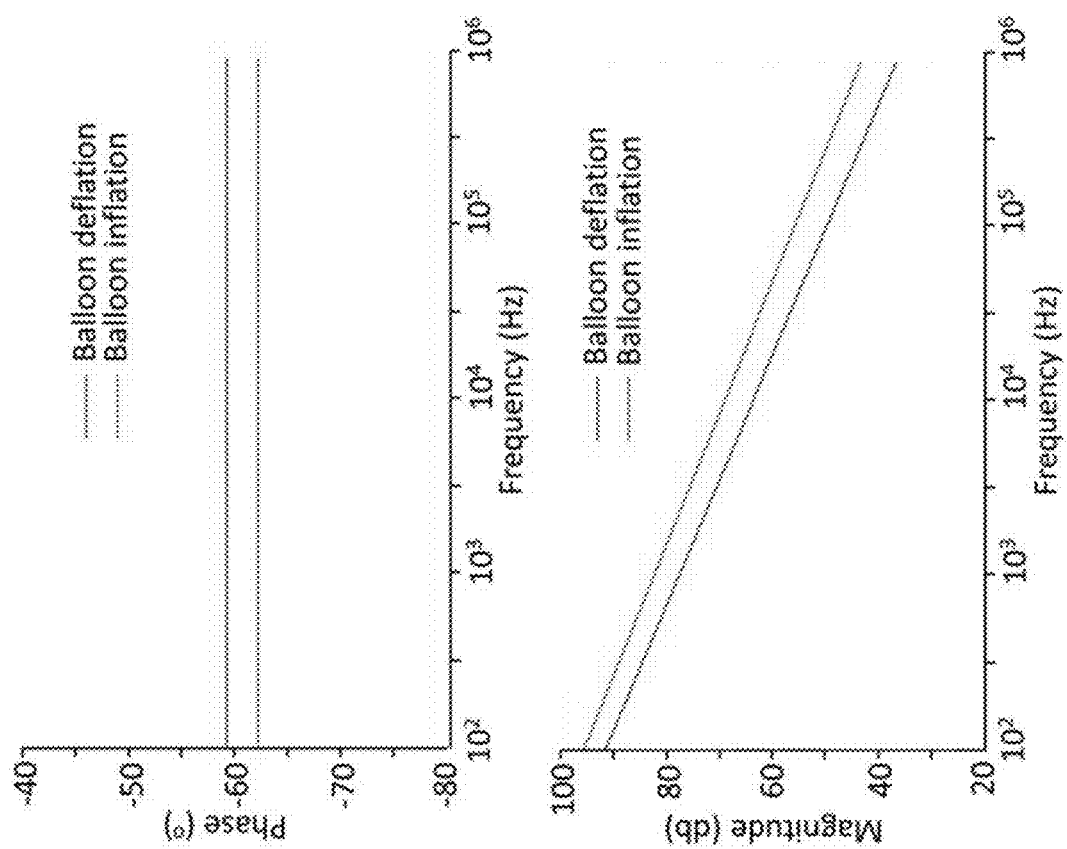
FIG. 18 is a Bode diagram (magnitude/phase) illustrating the behavior of the constant phase element under balloon deflation and inflation.

As shown above in Equation 3, Y denotes the empirical admittance value, and a is a constant between 0 and 1, $\omega$ is the angular frequency and $j=\sqrt{-1}$. Fitting from the two circuit models (FIG. 14G and FIG. 14H) yields two sets of Y and a: 321 nS·s^a/0.691 and 248 nS·s^a/0.659, for balloon deflation and inflation, respectively. A Bode diagram comparison of the two different constant phase elements is presented in FIG. 18 to show the behavior of the ZCPE, which is similar to that of a typical capacitance, i.e. being linear in magnitude and constant in phase. The value of a not being equal to 1 verifies the non-ideal capacitive behavior the electrode-tissue interface. The fitting results of other resistance and capacitance values are shown in FIG. 21A, as well as a physical model to compare the circuit model fitting with reported conductivity and permittivity of different tissues.

Data Analysis of 3-D EIS Measurements

Figures 17A, 17B, 17C:
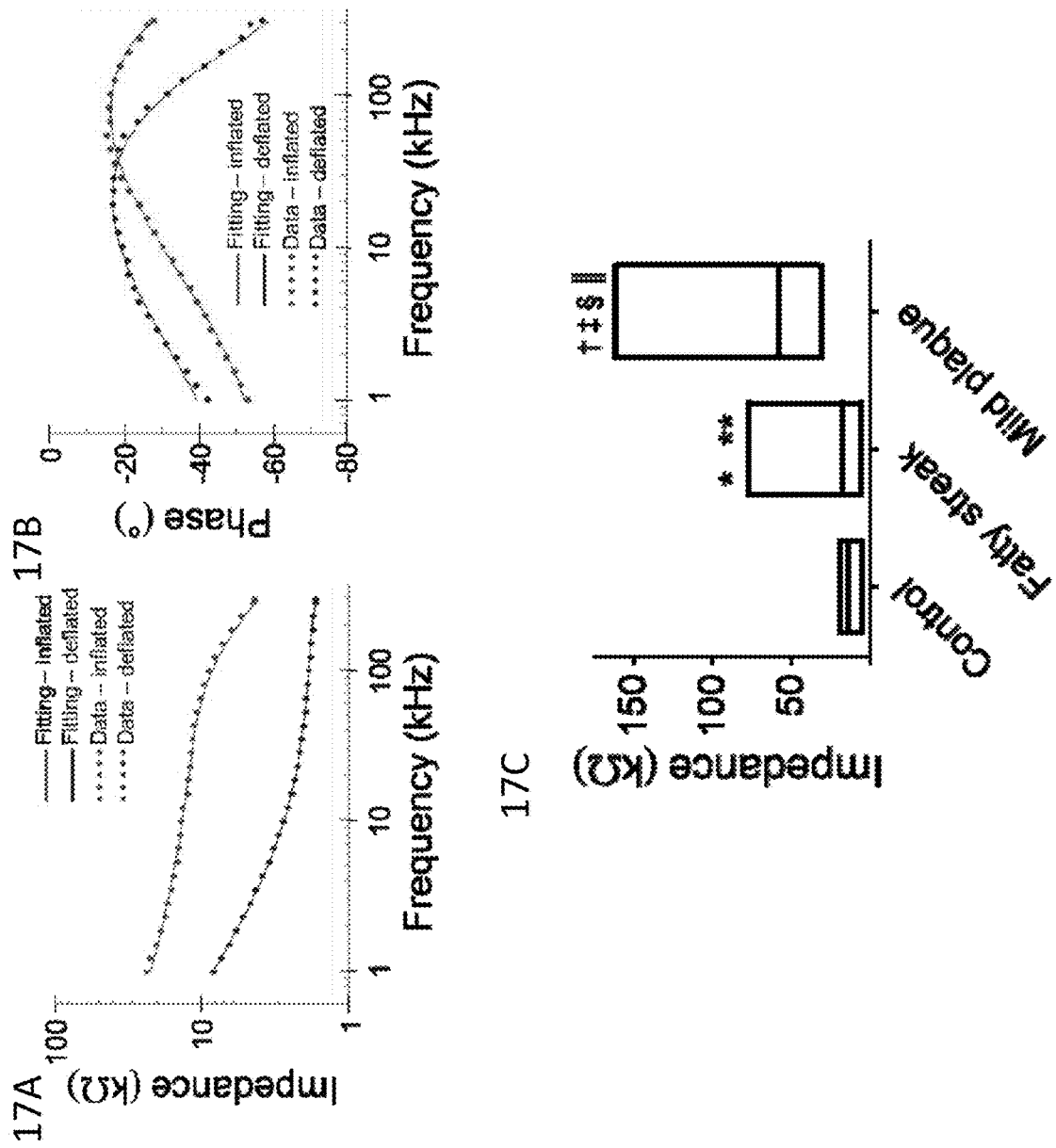
FIG. 17A though FIG. 17C depict a comparison between theoretical and experimental data. Representative data fitting was performed under balloon-deflation and -inflation (FIG. 17A, FIG. 17B). A simplex algorithm in the Gamry Echem Analyst software was used to demonstrate the EIS measurements by applying the two equivalent circuit models (shown in FIG. 14G, FIG. 14H). The fitting curves (solid lines) are in agreement with the experimental measurements (dotted lines) for impedance (FIG. 17A) and phase (FIG. 17B). In vivo data obtained at a frequency of 1 kHz demonstrates significant differences in the median and range (min-max) of impedance values by condition (FIG. 17C). Legend. *$P=0.016$ medians control vs. fatty streak. **$P=0.024$ value distributions control vs. fatty streak. †$P<0.001$ medians control vs. mild atherosclerotic plaque. ‡$P<0.001$ value distributions control vs. mild atherosclerotic plaque. § $P<0.001$ medians fatty streak vs. mild atherosclerotic plaque. ‖$P<0.001$ value distributions fatty streak vs. mild atherosclerotic plaque.

From each aortic interrogation point, the 15 permutations obtained at 1 kHz are displayed as the medians and the 2 extreme values (minimum-maximum) of the impedance range. These demonstrated a tight spread of values in control aortas, with a median impedance of 13.79 kΩ and a narrow range of global values ranging from a minimum of 5.22 kΩ to a maximum of 19.13 kΩ. Fatty streaks identified in the abdominal aorta at the level of renal artery bifurcation area or proximal to the aortic bifurcation demonstrated a median (17.75 kΩ) and range of values (minimum 5.79-maximum 77.05 kΩ) intermediate to values in control segments and to values in mild plaque segments from the thoracic aorta (median 58.32 kΩ, minimum 30.86 kΩ, maximum 16.17 kΩ) (FIG. 17C). There was a significant difference across groups (P<0.001) which was maintained when doing pairwise comparisons with correction for multiple testing. Comparing control to fatty streak, there was a significant difference in impedance medians (P=0.016) and value distributions (P=0.024) which was further accentuated when comparing control to mild atherosclerotic plaque (P<0.001 for differences in both medians and value distributions). The impedance differences between fatty streaks and mild atherosclerotic plaques were also highly significant (P<0.001 for differences in both medians and value distributions).

The presented novel 6-point configuration advances disease detection to flexible 3-D interrogation of early atherosclerotic lesions that harbor distinct electrochemical properties otherwise invisible by current imaging modalities such as invasive angiography. Atherosclerosis is a chronic inflammatory disease of the arterial wall resulting from a complex interplay between heritability (Kathiresan S, et al., Cell 148, 1242-1257 (2012)), environmental factors (Jackson S P, Nature Medicine 17, 1423-1436 (2011)), intestinal microbiota (Koeth R A, et al., Nature Medicine 19, 576-585 (2013)), biomechanical forces (Brown A J, et al., Nature Reviews Cardiology 13, 210-220 (2016)), and other causes. Atherosclerosis develops over decades (Libby P, New England Journal of Medicine 368.21 (2013): 2004-2013) with evidence of early lesions, or fatty streaks, present in autopsy series of young adults who died in their early 20s (Enos W F et al., Journal of the American Medical Association 152.12 (1953): 1090-1093). The end result of the advanced stages of the pathobiology of atherosclerosis remains a leading cause of mortality and morbidity worldwide through clinical manifestations such as acute coronary syndromes or strokes (Libby P, et al., Nature 473, 317-325 (2011)). Invasive coronary angiography is considered the gold standard of coronary artery disease determination. Whereas this technique permits visualization of established atherosclerotic plaques, it does not have the necessary spatial resolution to detect early stages of the disease (Dweck M R, et al., Nature Reviews Cardiology 13, 533-548 (2016)). Thus, 3-D EIS mapping provides the dielectric property at the electrode-tissue interface to detect metabolically active atherosclerotic lesions, albeit angiographically invisible, for possible early medical intervention and prevention of acute coronary syndromes or stroke.

Percutaneous transluminal coronary angioplasty (PTCA)—or balloon dilation of the coronary arteries—has been routinely performed for 40 years, initially as a stand-alone procedure (Grüntzig A, Percutaneous Vascular Recanalization. Springer Berlin Heidelberg, 1978. 57-65), and subsequently has been combined with coronary stent deployment (Sigwart U et al., New England Journal of Medicine 316.12 (1987): 701-706). The safety of balloon dilation of arteries to treat atherosclerotic lesions is well documented in humans (Indolfi C et al., Nature Reviews Cardiology (2016)) and experimental models (Iqbal J et al., Annals of biomedical engineering 44.2 (2016): 453-465), with success determined by a post-procedure angiogram (Levine G N et al., Circulation 124.23 (2011): e574-e651). Clinical application in humans of the 6-point EIS sensor would similarly require intravascular advancement of the catheter and verification of balloon inflation under angiographic guidance, with close monitoring of impedance characteristics to differentiate the distinct patterns obtained when the sensor is only in contact with blood (deflated, or not fully deployed) as opposed to the endoluminal vessel wall (inflated, or fully deployed) (FIG. 17A).

The novel 6-point configuration of the present study advances disease detection to 3-D interrogation of early atherosclerotic lesions that harbor distinct electrochemical properties otherwise invisible by current imaging modalities such as invasive angiography. The unique configuration allowed for three stretchable electrodes to be circumferentially and equidistantly positioned in individual rows, thereby generating 15 combinations of 2-point permutations for arterial wall EIS measurements. The elongated flexible polyimide electrodes eliminated the packaging challenge to connect the individual miniaturized contact pads with electrical wires for the 2-point sensors (Packard R R S, et al., Annals of Biomedical Engineering 44, 2695-2706 (2016)). The addition of active electrodes (from 2 to 6) engendered 15 different permutations to extend the EIS measurements from a focal region to an entire circumferential ring of the aorta. Data fitting results further demonstrate close agreement between the experimental EIS measurements and theoretical equivalent circuit modeling (FIG. 17A through FIG. 17C). Irrespective of the atherosclerotic lesion size and 3-D architecture, the 6-point configuration detected eccentric and small lesions, also known as fatty streaks, as validated by histology staining of atherosclerotic lesions (FIG. 16A through FIG. 16L, FIG. 17A through FIG. 17C). Thus, increased EIS measurements were detected in terms of impedance (2) in the non-obstructive lesions that occupied less than 5% of the luminal diameter, but harbored metabolically active lipids (FIG. 16A through FIG. 16L, FIG. 17A through FIG. 17C).

It is recognized that tissues store charges, and frequency-dependent electrical impedance (Z) develops in response to applied alternating current (AC). Previously proposed applications of EIS include assessment of cellular viability of human cancer cells (Hondroulis E et al., Theranostics (2014): 919-930) and amyloid β-sheet misfolding (Li H et al., Theranostics 4.7 (2014): 701). When an AC current is applied to the plaque in a vessel, a complex electric impedance (Z) is generated as a function of frequency. Z is defined as the summation of a real number (r) and the resistance ($X_c$) multiplied by the complex number (i) ($Z=r+X_c i$) (Yu F, et al., Biosensors and Bioelectronics 30, 165-173 (2011); Aroom K R, et al., Journal of Surgical Research 153, 23-30 (2009)). Fat-free tissue is known as a good electrical conductor for its high water (approximately 73%) and electrolytes content (ions and proteins), whereas fatty tissue is anhydrous and a poor conductor. Thus, these electrical properties synergistically render a significantly lower electrical conductivity in lipid-rich plaques ($\sigma^* = \sigma + i\omega\varepsilon$; $\sigma$, $\varepsilon$ being the intrinsic conductivity and permittivity of the tissue) than the rest of the blood and vascular components. Early stage lesions, though small in size and thus difficult to detect with conventional angiography, still exhibit a distinctive impedimetric behavior as opposed to normal arteries. These EIS properties have formed the electrochemical basis to detect early stage lipid-rich plaques.

Several distinct electrode configurations have been reported for intravascular impedimetric interrogation. Süselbeck et al. introduced a catheter-based 4-point electrode configuration to address the electrode-tissue contact impedance issue (Suselbeck T, et al., Basic Res Cardiol 100, 446-452 (2005)). However, its relatively large device dimension—required to accommodate 4 electrodes (2 cm in total length)—posed a clinical challenge for intravascular deployment (Suselbeck T, et al., Basic Res Cardiol 100, 446-452 (2005)). The 2-point concentric electrode configuration was previously demonstrated to provide a ~2000 fold reduction in device dimension (300 μm in diameter) to enable integration with different sensing modalities, including ultrasonic transducers and flow sensors (Yu F, et al., Biosensors and Bioelectronics 43, 237-244 (2013); Ma J, et al., Sensors and Actuators B: Chemical 235, 154-161 (2016)). Furthermore, the concentric configuration addressed the heterogeneous tissue composition, uneven surface topography and non-uniform current distribution of the atherosclerotic lesions. Recently, the 2-point electrode concept was introduced by implementing two identical flexible electrodes (240 μm in diameter) with a large separation (400 μm); thus, providing a deep current penetration for intraplaque burden detection (Packard R R S, et al., Annals of Biomedical Engineering 44, 2695-2706 (2016)).

Although 4-electrode systems can be miniaturized to become more suitable in clinical applications, they still occupy twice the space of 2-electrode systems. This issue further manifests itself when multiple measuring sites are required, as in the case of the 6-point configuration presented in the current study. There would be 12 electrodes needed to implement the equivalent for 4-electrode systems, thereby greatly complicating the possible electrode layout design as well as the electrical connections to the measurement instruments. Regarding the electrode-tissue interface impedance, as shown in FIG. 17A there is a clear shift of the impedance value throughout the frequency spectrum between balloon deflation and inflation. These impedance values are composed of the interface impedance as well as the tissues under interrogation, thereby indicating that the interface impedance is dominated by the tissue impedance. Hence, the impedance measurement reflects varying responses from the underlying tissues (atherosclerotic plaques, aorta, etc.) and can be utilized in evaluating different tissue compositions. It is worth noting that if the electrodes were to be further miniaturized, thereby increasing the electrode-tissue interface impedance, the tissue impedance might not be the dominating component in the 2-electrode system. Further treatment, e.g. electroplating platinum black onto the electrode to reduce the interface impedance, may be necessary to achieve high measurement specificity.

The aforementioned EIS sensing devices only focus on the local current detection that merely detects a small region of the entire endovascular segment where the atherosclerotic lesions are often eccentric and multiple. The present study advances EIS sensing by implementing the 6-point configuration to optimize 3-D detection of small, angiographically invisible, atherosclerotic lesions. This unique configuration allowed for six stretchable electrodes to be circumferentially and equidistantly positioned in individual rows around a dilatable balloon (FIG. 5A through FIG. 5D, FIG. 6A through FIG. 6E) and were deployed in vivo in the NZW rabbit model of atherosclerosis. Upon balloon inflation, all electrodes were made to be in contact with the endoluminal surface. The elongated flexible polyimide electrodes eliminated the packaging challenge to connect the individual miniaturized contact pads with electrical wires for the 2-point sensors (Packard R R S, et al., Annals of Biomedical Engineering 44, 2695-2706 (2016)). The addition of active electrodes (from 2 to 6) engendered 15 different permutations to extend the EIS measurements from a focal region to an entire circumferential ring of the aorta. Data fitting results using an equivalent circuit model further demonstrate close agreement between the experimental EIS measurements and theoretical equivalent circuit modeling (FIG. 17A through FIG. 17C). The fitting results are presented in FIG. 21A and a detailed physical modeling was further performed to demonstrate that the findings are in reasonable agreement with reported electrical properties of multiple tissues, thereby validating the simplified circuit model (FIG. 19A, FIG. 19B, FIG. 20A, FIG. 20B, FIG. 21B, FIG. 21C). The local EIS measurements were then reconstructed into 3-D impedimetric mapping (FIG. 15A through FIG. 15G) to significantly enhance the visualization quality and translational applicability of the impedance data.

Figures 19A, 19B:
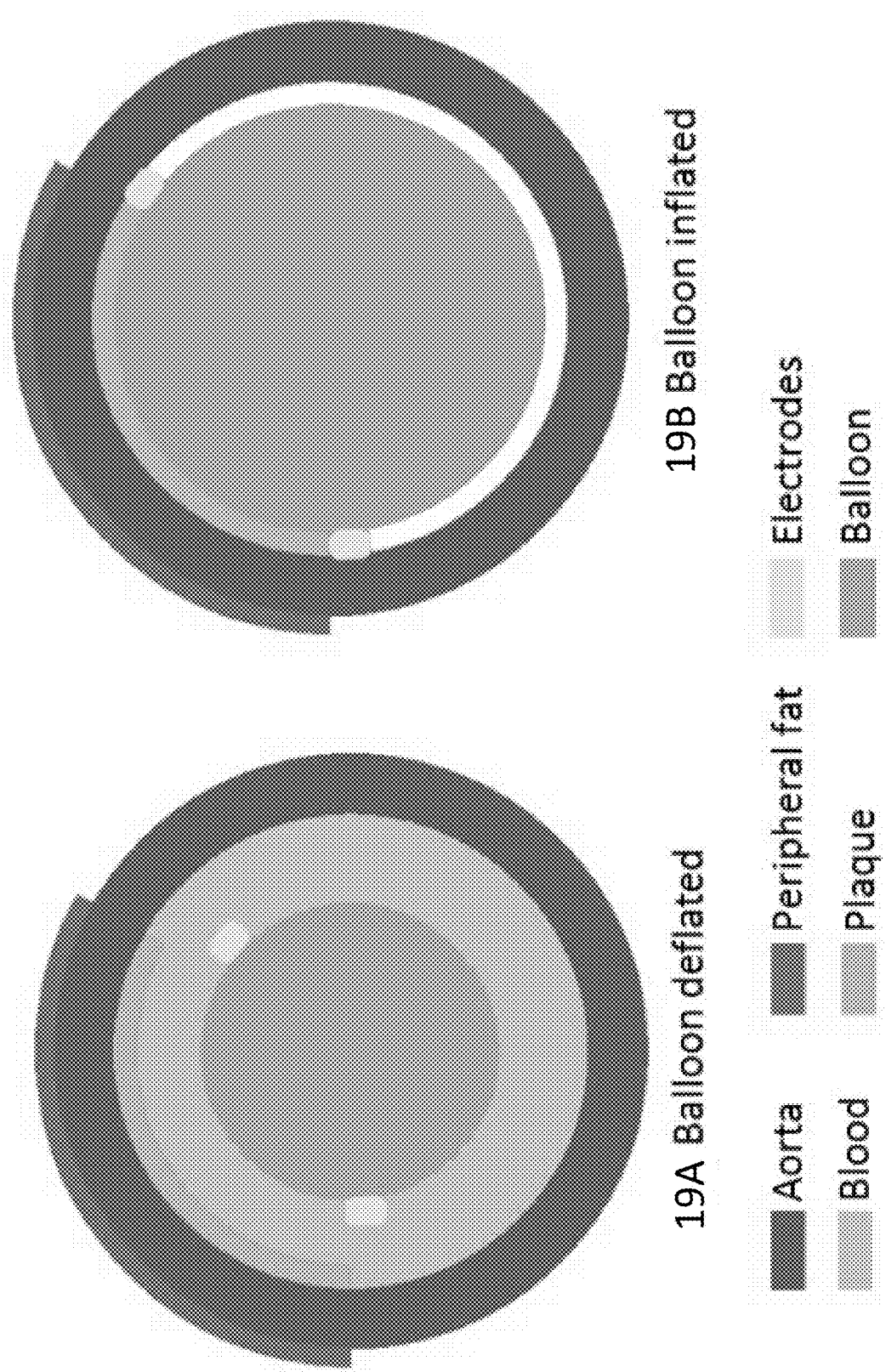
FIG. 19A and FIG. 19B are cross-sectional diagrams of in vivo electrode positioning with respect to the aortic cross-section under interrogation under balloon (FIG. 19A) deflated and (FIG. 19B) inflated conditions.
Figures 20A, 20B:
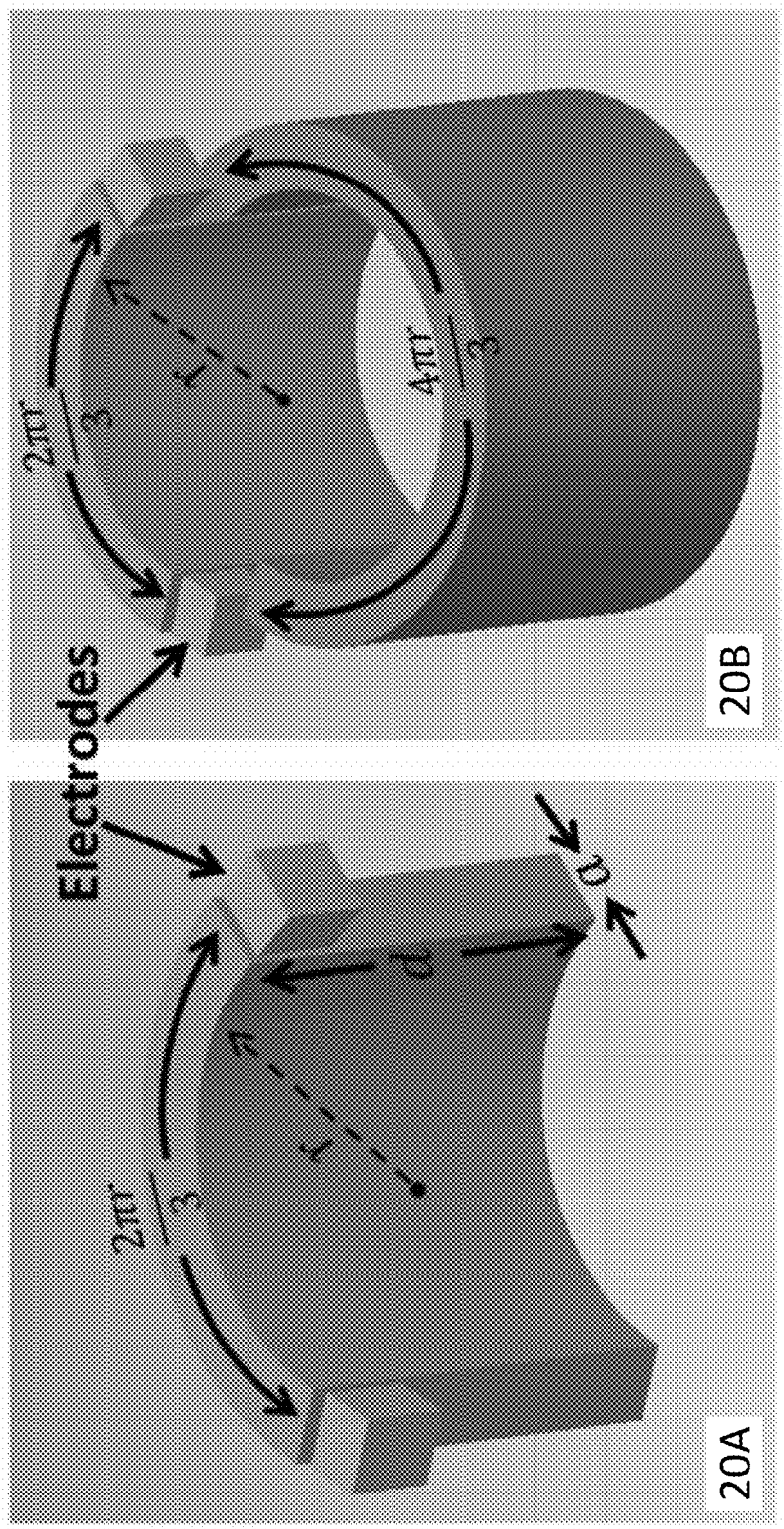
FIG. 20A and FIG. 20B are 3D renderings of tissue model impedance calculation parameters of the electrodes on the sensor (FIG. 20A) and the sensor in contact with the aorta (FIG. 20B).

The detailed physical modeling is described as follows. For each tissue type (blood, aorta, plaque, perivascular fat), the total impedance can be written based on the circuit model in FIG. 14G as:

$$Z = A - B \cdot j \tag{Eq. 9}$$

$$A = \frac{\omega^2 C^2 R_1 R_2 (R_1 + R_2) + R_1}{1 + \omega^2 C^2 (R_1 + R_2)^2} \tag{Eq. 10}$$

$$B = \frac{\omega C R_2^2}{1 + \omega^2 C^2 (R_1 + R_2)^2} \tag{Eq. 11}$$

where $\omega$ denotes the angular frequency, $j=\sqrt{-1}$, $R_1$, $R_2$, and C represent the two resistances and capacitance value from the circuit model. To demonstrate that the fitting results of all the resistance and capacitance (shown in FIG. 21A) from different tissues are reasonable, a physical model is presented that uses the intrinsic electrical properties and geometric factors of each tissue to obtain their impedance value, which will then be compared with the Z shown above. First, the cross-sectional schematics showing the relative position of electrodes and different tissues under either balloon inflation or deflation are depicted in FIG. 19A and FIG. 19B. The condition shown in FIG. 19A corresponds to the circuit model presented in FIG. 14G and will be utilized for validating the parameters for blood. The scenario in FIG. 19B (modeled as FIG. 4H) is considered for aorta wall, plaque, and perivascular fat as the dimension of blood is difficult to estimate when the balloon is inflated. For plaque and perivascular fat, a simple impedance model can be considered, as shown in FIG. 20A. The impedance of the tissue can be written as (Sun T et al., Langmuir 26.6 (2009): 3821-3828):

$$Z' = \frac{1}{j\omega\varepsilon * G} \tag{Eq. 12}$$

where ε* represents the complex permittivity:

$$\varepsilon^* = \varepsilon\varepsilon_0 - \frac{j\sigma}{\omega} \quad \text{(Eq. 13)}$$

where σ, ε denotes the conductivity and relative permittivity of the tissue, $\varepsilon_0$=8.85e-12 F/m the vacuum permittivity, and G=ad/l the geometric factor. For plaque and perivascular fat, the scenario in FIG. 20A is considered, and based on the histology image in FIG. 14E and FIG. 14F, the estimate of l=2πr/3 can be made. Note that the electrode pair shown in FIG. 20A and FIG. 20B is separated by ⅓ of the circumference due to the design (see FIG. 5A through FIG. 5D). For blood and the aorta wall (as a complete circular object), the scenario shown in FIG. 20B is considered, where ⅓ of the tissue is in parallel with the remaining ⅔, therefore yielding an effective l=4πr/9. From Eq. 12 and Eq. 13, the impedance value of each tissue can be obtained merely based on their intrinsic electrical properties and geometrical variables:

$$Z' = A' - B' \cdot j \quad \text{(Eq. 14)}$$

$$A = \frac{\sigma l}{ad(\sigma^2 + \omega^2(\varepsilon\varepsilon_0)^2)} \quad \text{(Eq. 15)}$$

$$B = \frac{\omega\varepsilon\varepsilon_0 l}{ad(\sigma^2 + \omega^2(\varepsilon\varepsilon_0)^2)} \quad \text{(Eq. 16)}$$

Z is calculated using the fitting results, and Z' is achieved through the electrical properties of different tissues and geometric variables estimated from the histology image (as shown in FIG. 14A through FIG. 14H). The value ω=10 kHz was chosen for all of the calculations. FIG. 21A shows the achieved resistance and capacitance values for each of the tissues obtained from fitting. FIG. 21B lists all of the parameters used in the calculation. FIG. 21C shows the comparison between the results obtained from the circuit model and the results from the physical model (A,',B'). As is evident, results from the two sets of calculation are all within an order of magnitude of each other. The source of discrepancy could rise from: a) the irregularity of the actual tissue geometry as compared to the simple geometry used in the calculation; b) there is a relatively wide range of reported electrical property values of individual tissues, e.g. the conductivity of fat varies around 3-5 fold in the published literature (Awada K A et al., IEEE Transactions on Biomedical Engineering 45.9 (1998): 1135-1145; Gabriel C et al., Physics in medicine and biology 41.11 (1996): 2231; Hasgall P A et al., "IT'IS Database for thermal and electromagnetic parameters of biological tissues. Version 2.6, Jan. 13, 2015." (2015)). In conclusion, the presented circuit model can reasonably describe the actual electrical behavior of the multiple existing tissues.

The present study demonstrates that the impedance value distribution obtained from different combinations of the 6-point electrodes at a frequency of 1 kHz exhibits a significantly wider range in aortas of high-fat diet fed rabbits compared to controls on a normal diet (FIG. 17C). This finding signifies a major characteristic shift from healthy arteries to ones with subclinical atherosclerosis and therefore can serve as a detection criterion. The wider range of impedance value arises from the fact that the existence of eccentric and multiple atherosclerotic lesions around the endoluminal surface increases the overall impedance variation compared to a homogeneous healthy artery. Previously designed EIS devices (Yu F, et al., Biosensors and Bioelectronics 30, 165-173 (2011); Streitner I, et al., Atherosclerosis 206, 464-468 (2009); Suselbeck T, et al., Basic Res Cardiol 100, 446-452 (2005); Packard R R S, et al., Annals of Biomedical Engineering 44, 2695-2706 (2016)) interrogated only limited segments of the vessel, potentially missing lesions that are not in close proximity with the electrodes. Therefore, the present new 6-point configuration permits comprehensive 3-D mapping and successful detection of eccentric and small atherosclerotic lesions that harbor metabolically active lipids (FIG. 16A through FIG. 16L, FIG. 17A through FIG. 17C), however remain invisible with conventional angiography (FIG. 14B through FIG. 14D).

In summary, a novel 6-point electrode design is introduced for early detection of subclinical atherosclerotic lesions. The unique electrode configuration allows for 3 stretchable electrodes to be circumferentially and equidistantly positioned in individual layers. The 15 EIS permutations provide a paradigm shift, allowing the reconstruction of a 3-D map of impedance spectroscopy. In this context, metabolically active plaques, also known as fatty streaks, have been identified that harbor lipid-laden macrophage foam cells (Yu F, et al., Annals of Biomedical Engineering 39, 287-296 (2011); Yu F, et al., Biosensors and Bioelectronics 43, 237-244 (2013); Packard R R S, et al., Annals of Biomedical Engineering 44, 2695-2706 (2016); Cao H, et al., Biosensors and Bioelectronics 54, 610-616 (2014)) that are otherwise non-detectable by current angiography. Thus, 3-D EIS mapping holds translational promises for early detection and prevention of acute coronary syndromes or strokes.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A tissue sensing device comprising:
    a first catheter comprising a lumen, a closed distal end, and an open proximal end;
    a second catheter comprising a lumen, a distal end, and an open proximal end;
    at least one ultrasound transducer positioned within the first catheter lumen near the closed distal end;
    an expandable element near the distal end of the second catheter; and
    a sensor positioned on the expandable element;
    wherein the at least one ultrasound transducer of the first catheter is positioned distal to the expandable element of the second catheter.

2. The device of claim 1, wherein the first catheter lumen and the second catheter lumen are adjacent and parallel to each other.

3. The device of claim 1, wherein the first catheter and the second catheter are co-axial, wherein the first catheter is at least partially enveloped in the lumen of the second catheter, and wherein the first catheter extends past the distal end of the second catheter.

4. The device of claim 3, wherein the distal end of the second catheter forms a seal with the first catheter such that a length of the first catheter extends past the distal end of the second catheter.

5. The device of claim 1, wherein the lumen of the first catheter is filled with a fluid.

6. The device of claim 1, wherein the at least one ultrasound transducer is attached to a distal end of a torque wire.

7. The device of claim 6, wherein the at least one ultrasound transducer is rotatable within the lumen of the first catheter.

8. The device of claim 1, wherein the expandable element is a balloon.

9. The device of claim 1, wherein the sensor is an electrochemical impedance spectroscopy (EIS) sensor.

10. The device of claim 9, wherein the EIS sensor comprises a two-point electrode.

11. The device of claim 1, wherein the first catheter comprises an inner diameter between about 0.5 and 2 mm.

12. The device of claim 1, wherein the second catheter comprises an inner diameter between about 1 and 3 mm.

13. The device of claim 8, wherein the balloon can be inflated to a diameter between about 1 and 15 mm.

14. The device of claim 8, wherein the balloon lies flush with the diameter of the second catheter when deflated.

15. The device of claim 1, further comprising at least one pressure sensor, at least one temperature sensor, at least one flow sensor, or any combination thereof.

16. A method of characterizing a tissue region of interest, comprising the steps:
    positioning the device of claim 1 near a tissue;
    imaging the tissue with an ultrasound transducer on the device to locate a region of interest;
    positioning the device such that the sensor on the device faces the region of interest;
    touching the sensor of the device to the region of interest by expanding the expandable element on the device;
    measuring impedance of the region of interest with the sensor; and
    characterizing the region of interest based on the measured impedance.

17. The method of claim 16, wherein the sensor is an EIS sensor.

18. The method of claim 17, wherein the EIS sensor measures impedance by driving an AC current through the region of interest.

19. The method of claim 18, wherein the AC current is driven with a voltage between about 10 and 100 mV.

20. The method of claim 18, wherein an impedance spectrum is obtained by measuring current over a frequency sweep between about 100 Hz and 5 MHz.

21. The method of claim 16, wherein the region of interest is an atheroma.

22. The method of claim 21, wherein an impedance that is associated with an atheroma indicates a high level of oxidized low density lipoprotein (oxLDL) and macrophage/foam cells present in the atheroma.

23. The method of claim 22, wherein the impedance that is associated with an atheroma is indicative of a high risk of atheroma rupture.

24. The device of claim 1, wherein the first catheter is configured to rotate independently from the second catheter.

25. The device of claim 1, wherein the sensor comprises a 6-point electrode configuration EIS sensor.

26. The device of claim 25, wherein the device comprises fifteen EIS sensor permutations.

27. The device of claim 26, wherein the EIS permutations comprise three 2-point electrodes vertically linked between two rows, six 2-point electrodes circumferentially linked within rows, and six 2-point electrodes cross-linked diagonally between the two rows.

28. The device of claim 25, wherein the device is configured to perform flexible 3-dimensional interrogation and impedimetric mapping of an arterial segment over a plurality of rings or sub-segments.

* * * * *